United States Patent
Helal et al.

(10) Patent No.: US 12,135,281 B2
(45) Date of Patent: Nov. 5, 2024

(54) METHOD OF DETECTING MERCURY IONS WITH A FLUORESCEIN HYDRAZIDE-APPENDED METAL-ORGANIC FRAMEWORK AS A CHEMOSENSOR

(71) Applicant: KING FAHD UNIVERSITY OF PETROLEUM AND MINERALS, Dhahran (SA)

(72) Inventors: Aasif Helal, Dhahran (SA); Muhammed Naeem, Dhahran (SA); Mohammed Fettouhi, Dhahran (SA); Md. Hasan Zahir, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 399 days.

(21) Appl. No.: 17/840,045

(22) Filed: Jun. 14, 2022

(65) Prior Publication Data
US 2023/0400409 A1  Dec. 14, 2023

(51) Int. Cl.
*G01N 21/35* (2014.01)
*G01N 21/3577* (2014.01)
*G01N 21/17* (2006.01)

(52) U.S. Cl.
CPC ... *G01N 21/3577* (2013.01); *G01N 2021/174* (2013.01)

(58) Field of Classification Search
CPC ............. G01N 21/3577; G01N 2021/174
See application file for complete search history.

(56) References Cited

U.S. PATENT DOCUMENTS

| | | | |
|---|---|---|---|
| 7,824,473 | B2 | 11/2010 | Mirkin et al. |
| 11,124,522 | B2 | 9/2021 | Helal |
| | | (Continued) | |

FOREIGN PATENT DOCUMENTS

| | | |
|---|---|---|
| CN | 102419310 B | 4/2013 |
| CN | 107245334 A | 10/2017 |
| CN | 111398396 A | 7/2020 |
| | (Continued) | |

OTHER PUBLICATIONS

Aasif Helal, et al., "Fluorescein Hydrazide-Appended Metal-Organic Framework as a Chromogenic and Fluorogenic Chemosensor for Mercury Ions", Molecules, vol. 26, Issue 5773, Sep. 23, 2021, pp. 1-13.
(Continued)

*Primary Examiner* — Nicole M Ippolito
(74) *Attorney, Agent, or Firm* — Oblon, McClelland, Maier & Neustadt, L.L.P.

(57) ABSTRACT

A method of detecting $Hg^{2+}$ ions in an aqueous solution is described. The method includes contacting the aqueous solution with a metal-organic framework (MOF) chemosensor composite to form a mixture and monitoring a change in an absorption and/or a fluorescence profile of the MOF chemosensor composite in the mixture to determine a presence or absence of $Hg^{2+}$ ions in the aqueous solution. The MOF chemosensor composite includes fluorescein hydrazide (FH); and a MOF, including nickel as a metal ion and at least one trimesic acid (BTC) ligand. A hydrazide group on the fluorescein hydrazide coordinates to the metal ion of the MOF.

17 Claims, 28 Drawing Sheets

(56) References Cited

U.S. PATENT DOCUMENTS

2019/0345171 A1* 11/2019 Ma .................... B01J 20/3206
2022/0144859 A1* 5/2022 Peedikakkal ......... C07F 15/045

FOREIGN PATENT DOCUMENTS

CN   113817466 A   12/2021
KR   10-2010-0019906 A   2/2010

OTHER PUBLICATIONS

Yun Shu, et al., "Incorporation of perovskite nanocrystals into lanthanide metal-organic frameworks with enhanced stability for ratiometric and visual sensing of mercury in aqueous solution", Journal of Hazardous Materials, vol. 430, May 15, 2022, 3 pages (Abstract only).

* cited by examiner

METHOD OF DETECTING MERCURY IONS WITH A FLUORESCEIN HYDRAZIDE-APPENDED METAL-ORGANIC FRAMEWORK AS A CHEMOSENSOR

STATEMENT OF PRIOR DISCLOSURE BY AN INVENTOR

Aspects of the present disclosure are described in A. Helal, M. Naeem, M. Fettouhi, Md. H. Zahir. "Fluorescein Hydrazide-Appended Metal—Organic Framework as a Chromogenic and Fluorogenic Chemosensor for Mercury Ions", Sep. 23, 2021; Molecules; 26; 5773. incorporated herein by reference in its entirety.

BACKGROUND

Technical Field

The present disclosure is directed to a method of detecting mercury ions, and particularly to a method of detecting mercury ions with a fluorescein hydrazide-appended metal-organic framework.

Description of Related Art

The "background" description provided herein is to present the context of the disclosure generally. Work of the presently named inventors, to the extent described in this background section, and aspects of the description that may not otherwise qualify as prior art at the time of filing, are neither expressly nor impliedly admitted as prior art against the present invention.

Mercury is considered to be a highly toxic heavy metal and non-biodegradable pollutant. It is bio-accumulated throughout the food chain due to its water stability, non-degradability, and physiological toxicity. The noxious nature of $Hg^{2+}$ is due to its high binding affinity for the amino ($-NH_2$) and thiol ($-SH$) groups of proteins, which have antagonistic effects on the immune system, digestive system, chromosomes, kidney function, pulmonary system, and central nervous system. Several analytical techniques are available for the detection of mercury, such as atomic absorption spectroscopy (AAS), inductively coupled plasma atomic emission spectrometry (ICP-AES), and inductively coupled plasma mass spectrometry (ICP-MS). However, these methods are expensive, involve complex instruments with well-established infrastructures, and require sample pre-treatment that is laborious, time-consuming, and associated with a high risk of contamination and sample loss. Thus, these methods are unsuitable for in situ or instant analysis during field studies. Several sensors based on organic compounds, nanoparticles, polymeric materials, proteins, magnetic nano-composites, and DNA-functionalized hydrogels have been used to detect mercury in the past. However, these materials suffer from one or more drawbacks including poor thermal and chemical stability, multistep synthesis, selectivity, and sensitivity.

In recent years, metal-organic frameworks (MOFs), which are extended porous crystalline structures, have been used due to their crystalline nature, high porosity, tunable pores (microporous and mesoporous), and moderately high stability for detection of different analytes. However, there still exists a need to develop composites for detecting $Hg^{2+}$ ions in a cost effective and efficient manner.

SUMMARY

In an exemplary embodiment, a method of detecting $Hg^{2+}$ ions in an aqueous solution is described. The method includes contacting the aqueous solution with a metal-organic framework (MOF) chemosensor composite to form a mixture and monitoring a change in an absorption and/or a fluorescence profile of the MOF chemosensor composite in the mixture to determine a presence or absence of $Hg^{2+}$ ions in the aqueous solution. The MOF chemosensor composite includes fluorescein hydrazide (FH); and a MOF, with nickel as a metal ion and at least one trimesic acid (BTC) ligand. A hydrazide group on the fluorescein hydrazide coordinates to the metal ion of the MOF.

In some embodiments, a unit of the MOF chemosensor composite has a formula of $[Ni_3(BTC)_2(H_2O)_{3-n}(FH)_n]$, where n=1, 2 or 3.

In some embodiments, at least 90% of the nickel is $Ni^{2+}$.

In some embodiments, the MOF chemosensor composite has a morphology of rod-shaped structures assembled into sheets.

In some embodiments, the MOF chemosensor composite has a Brunauer-Emmett-Teller (BET) specific surface area of 350-450 square meters per gram ($m^2g^{-1}$).

In some embodiments, the MOF chemosensor composite has stability up to 150° C.

In some embodiments, the MOF has at least one pore and wherein the fluorescein hydrazide at least partially penetrates at least one pore of the MOF.

In some embodiments, the method further includes monitoring the change in the absorption profile of the MOF chemosensor composite between 350 and 600 nanometers (nm), where a peak of the profile between 350 and 380 nm decreases in intensity and a peak between 550 and 600 nm increases in intensity in the presence of $Hg^{2+}$.

In some embodiments, the method further includes monitoring the change in the fluorescence profile of the MOF chemosensor composite between 500 and 650 nm, where a peak of the profile between 515 and 550 nm increases in intensity in the presence of $Hg^{2+}$.

In some embodiments, the change in the absorption and/or fluorescence profile linearly correlates with the concentration of $Hg^{2+}$ in the aqueous solution.

In some embodiments, the method further includes quantifying the change in the absorption and/or fluorescence profile to determine a concentration of $Hg^{2+}$ ions in the aqueous solution.

In some embodiments, the aqueous solution further includes at least one metal cation selected from the group consisting of $Na^+$, $K^+$, $Ca^{2+}$, $Mg^{2+}$, $Sr^{2+}$, $Rb^{2+}$, $Cs^{2+}$, $Al^{3+}$, $Ga^{3+}$, $Fe^{2+}$, $Fe^{3+}$, $Cu^{2+}$, $Ni^{2+}$, $Pb^{2+}$, $Cd^{2+}$, $Co^{2+}$, $Zn^{2+}$, $Pd^{2+}$, and $Ag^+$. The change in the absorption and/or fluorescence profile occurs only in the presence of $Hg^{2+}$.

In some embodiments, the MOF chemosensor composite is selective for detecting $Hg^{2+}$ ions.

In some embodiments, the detection limit (LOD) for $Hg^{2+}$ ions is 1-10 parts per billion (ppb).

In some embodiments, the binding constant of the $Hg^{2+}$ to the MOF chemosensor composite is $10^5$-$10^6$ $M^{-1}$.

In some embodiments, the method includes adding ethylenediaminetetraacetic acid to the mixture to form a solution, filtering the solution, and drying at a temperature of 80-120° C. for at least one hour to form a recovered MOF chemosensor composite.

In some embodiments, the recovered MOF chemosensor composite maintains at least 90% of the crystallinity of the MOF chemosensor composite.

The preceding general description of the present illustrative disclosure and the following detailed description thereof are merely exemplary aspects of the teachings of this disclosure and are not restrictive.

BRIEF DESCRIPTION OF THE DRAWINGS

A complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
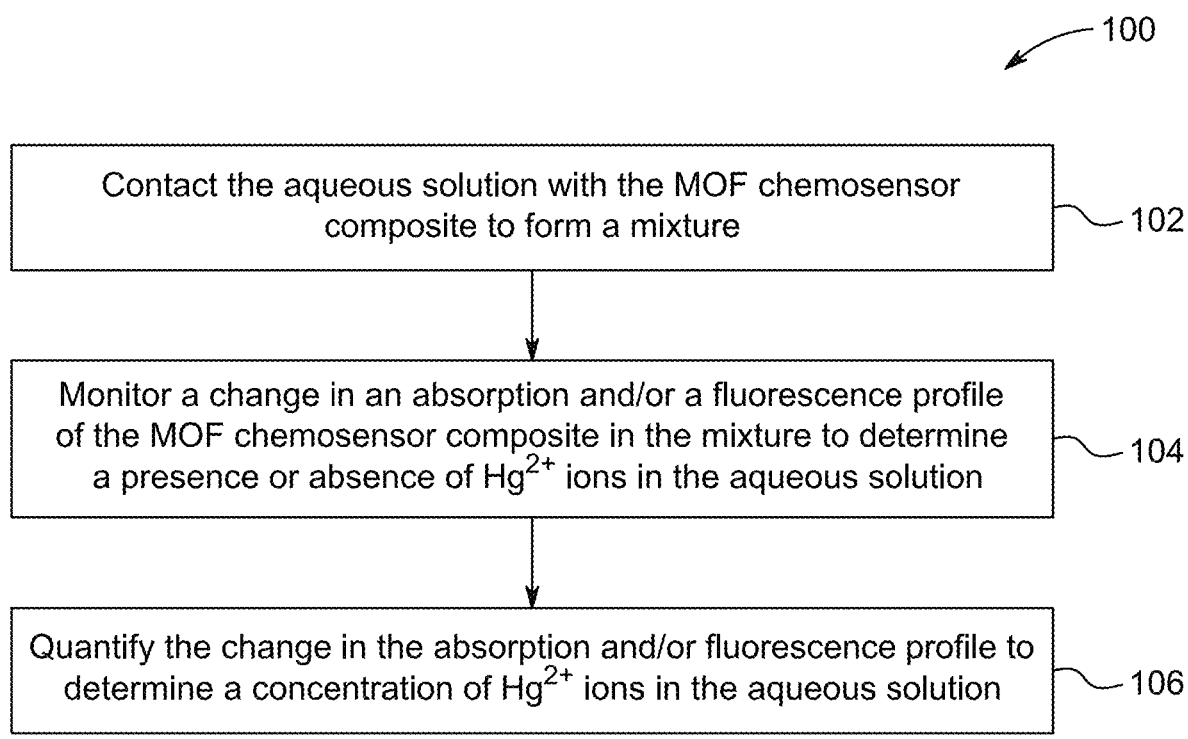
FIG. 1 is a flow chart depicting a method for detecting $Hg^{2+}$ ions, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

The term "carboxylic acids" or "carboxylic acid compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) at least one functional group of formula —COOH, or (b) at least one moiety having at least one functional group of formula —COOH. Non-limiting examples of di-carboxylic acids include benzoic acid, 3-carboxy-1,2,4-triazole, 5-carboxy-1,2,4-triazole, 4-carboxy-1,2,3-triazole, 5-carboxy-1,2,3-triazole, 5-carboxytetrazole, 2-carboxy-1,3,5-triazine, 3-carboxy-1,2,4-triazine, 5-carboxy-1,2,4-triazine, 6-carboxy-1,2,4-triazine, and like.

The term "hydrazide" refers to a function group of formula R—NH—$NH_2$ where R is acyl (R'CO—), sulfonyl (R'$SO_2$—), or phosphoryl (R'$_2$P(O)—) group.

As used herein "metal-organic frameworks" or MOFs are compounds having a lattice structure made from (i) a cluster of metal ions as vertices ("cornerstones") ("secondary building units" or SBUs) which are metal-based inorganic groups, for example metal oxides and/or hydroxides, linked together by (ii) organic linkers. The linkers are usually at least bidentate ligands which coordinate to the metal-based inorganic groups via functional groups such as carboxylates and/or amines. MOFs are considered coordination polymers made up of (i) the metal ion clusters and (ii) ligand building blocks.

Aspects of the present disclosure are directed towards a metal-organic framework chemosensor composite, or a "composite" of fluorescein hydrazide coordinately bonded to the nickel SBU of a nickel-based MOF. The prepared composite was well-characterized by powder X-ray diffractogram (PXRD), nitrogen adsorption ($N_2$) isotherm, Fourier Transform Infrared (FT-IR), thermogravimetric analysis (TGA), field emission scanning electron microscope (FE-SEM), and X-ray photoelectron spectroscopy (XPS). The composite was further evaluated for its performance in the optical detection of heavy metals. The results indicate that the composite of the present disclosure acts as a chromogenic and fluorogenic sensor for detecting mercury ions selectively in a rapid, cost-effective, and efficient manner.

In an embodiment, the composite includes a MOF. The MOF of the present disclosure is preferably based on nickel ions (made from nickel ion clusters), referred to herein as a nickel metal-organic framework (Ni-MOF). The Ni-MOF herein is intended to cover any MOF which contains predominantly nickel ions with respect to the total metal ion content. The Ni-MOFs of the disclosure include nickel ion clusters (cornerstones) which are nickel inorganic groups, typically nickel ions connected by bridging oxygen groups, bridging hydroxide groups, or both. These nickel ion clusters are further coordinated to at least one linker. In some cases, the nickel ion clusters may be further connected to non-bridging modulator species, complexing reagents or ligands (e.g., sulfates or carboxylates such as formate, benzoate, acetate, etc.) and/or solvent molecules (e.g., $H_2O$). The idealized nickel ion cluster is considered to be a hexanuclear nickel ion cluster based on an octahedron of nickel ions ($Ni^{2+}$) which are µ3-bridged by $O^{2-}$ and/or $OH^-$ ions via the faces of the octahedron and further saturated by coordinating ligands containing oxygen atoms like carboxylate groups. However, in practice, there is a degree of flexibility in the structure of the nickel ion cluster. In an embodiment, the nickel in the MOF can exist in oxidation states −1, 0, +2, +3, and +4, or any combinations thereof. In a preferred embodiment, the nickel exists in a +2-oxidation state or as $Ni^{2+}$ ions. In an embodiment, at least 90%, preferably 95%, or 100% of the nickel is in the form of $Ni^{2+}$.

In addition to the nickel ion clusters (cornerstones), the Ni-MOFs of the present disclosure are formed from at least one linker, or ligand, which may be bidentate, tridentate, or tetradentate, and which links together adjacent nickel ion clusters to form the coordinated network. In an embodiment, at least one linker is a 5- or 6-membered carbocyclic ring substitute with at least two carboxylic acid groups. In an embodiment, at least one linker is a 5- or 6-membered carbocyclic ring substitute with three carboxylic acid groups. In an embodiment, at least one linker is trimesic acid (BTC). In an embodiment, at least one linker is a coordinating solvent. In an embodiment, the coordinating solvent may be at least one of but not limited to, water, dimethylformamide (DMF), dimethylsulfoxide (DMSO), dimethylacetamide (DMA), and acetonitrile ($CH_3CN$). In an embodiment, there are at least 2 different linkers. In an embodiment, the linkers include both water and BTC.

The metal ion and the ligand complex may be bound together to form the MOF. In an embodiment, a unit of the MOF has a formula of $[Ni_w(linker)_x(linker\ 2)_y(linker\ 3)_z]$. In an embodiment, a unit of the MOF has a formula of $[Ni_3(linker)_x(linker\ 2)_y(linker\ 3)_z]$, wherein x+y+z=5. In an embodiment, the ligands coordinated to the SBU are trimesic acid and water and a unit of the MOF has a formula of $[Ni_3(BTC)_2(H_2O)_3]$. In an embodiment, the MOF is solvated by additional solvents. In an embodiment, the additional solvents may be at least one of but not limited to, water, dimethylformamide (DMF), dimethylsulfoxide (DMSO), dimethylacetamide (DMA), and acetonitrile ($CH_3CN$). In an embodiment, the MOF has both DMF and water as solvating solvents with a formula of $[Ni_3(BTC)_2(H_2O)_3]\cdot(DMF)_3(H_2O)_3$.

The composite further includes a fluorescent dye. Optionally, the composite may consist of different molecular building units, such as organic dyes, fluorescent dyes, metal nanoparticles, and carbon quantum dots, which are loaded or coated inside or on the surface of MOFs to realize fluorescence sensing for specific anions and small molecules. In a preferred embodiment, the composite includes fluorescein hydrazide (FH) as the fluorescent dye. The fluorescent dye may be loaded or coated inside or on the surface of MOFs to realize fluorescence sensing for $Hg^{2+}$ ions. The FH has a hydrazide group that coordinates with the metal ion in the MOF to form the composite. In an embodiment, the hydrazide group of the FH is an acylhydrazide. In an embodiment, the MOF is heated to a temperature of 100-200° C., prior to the incorporation of the fluorescent dye, to remove at least some of a coordinated solvent ligands, particularly water ligands. In an embodiment, the FH replaces at least some of the previously coordinated water ligands. In an embodiment, the composite has a formula of $[Ni_3(BTC)_2(H_2O)_{3-n}(FH)_n]$, wherein n=1, 2 or 3. In a preferred embodiment, the unit of MOF has the formula $[Ni_3(BTC)_2(H_2O)_{3-n}(FH)_n]$, where n=1, labeled as FH@Ni(MOF).

In an embodiment, the composite has a morphology of rod-shaped structures assembled into sheets. In an embodiment, the rods have a width of 10-1,000 nm, preferably 100-900 nm, 200-800 nm, 300-700 nm, 400-600 nm, or approximately 500 nm. The properties of the composite can be altered by altering the porosity, surface area, or pore size of the ligand. In an embodiment, the MOF has at least one pore in which the FH partially penetrates. In an embodiment, the FH penetrates all pores of the MOF. In an embodiment, the FH penetrates at least 20% of the MOF pore, preferably 30%, 40%, 50%, 60%, 70%, 80%, 90%, or 100%. In an embodiment, the FH completely penetrates through the pore of the MOF. In an embodiment, the composite has a Brunauer-Emmett-Teller (BET) specific surface area of 350-450 $m^2g^{-1}$, preferably 375-425 $m^2g^{-1}$, or approximately 400 $m^2g^{-1}$. In an embodiment, the surface area of the composite compared to that of the MOF is significantly smaller due to the presence of the FH in the pores. In an embodiment, the composite has a stability up to 150° C., preferably 100-150° C., 110-140° C., or 120-130° C.

Referring to FIG. 1, a schematic flow diagram of the method of detecting $Hg^{2+}$ ions in an aqueous solution is illustrated. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes contacting the aqueous solution with the MOF chemosensor composite to form a mixture. In an embodiment, the aqueous solution can be drinking water, industrial wastewater, tap water, groundwater, river water, runoff streams, and static water bodies such as storage water. In an embodiment, the composite is contacted with the aqueous solution at a temperature range of 15-45° C., preferably 20-40° C., 25-35° C., or approximately 30° C. In an embodiment, the contacting occurs by pouring a solution of the composite into the aqueous solution. In an embodiment, the contacting occurs by adding a powder form of the composite into the aqueous solution. In an embodiment, the composite is mixed into the aqueous solution by a method such as but not limited to, manually stirring, using a stir bar, or a probe sonicator. In an embodiment, the composite is 0.1-1 mg/mL in the aqueous solution, preferably 0.3-0.8 mg/mL, or approximately 0.5 mg/mL.

At step 104, the method 100 includes monitoring a change in absorption and/or a fluorescence profile of the MOF chemosensor composite in the mixture to determine the presence or absence of $Hg^{2+}$ ions in the aqueous solution. A change in absorption or fluorescent profile is indicative of the presence of $Hg^{2+}$ ions in the aqueous solution. In contrast, no change in the absorption or fluorescent profile is indicative of the absence of $Hg^{2+}$ ions in the aqueous solution. This change can be monitored with a UV-Vis spectrometer, or a spectrofluorometer. In an embodiment, the change in the absorption and/or fluorescence profile linearly correlates with the concentration of $Hg^{2+}$ in the aqueous solution. In other words, the greater the change, the higher the concentration of the $Hg^{2+}$ ions in the aqueous solution.

In an embodiment, the method includes monitoring the change in the absorption profile of the MOF chemosensor composite between 350 and 600 nm, preferably 400-550 nm, or approximately 500 nm. In some embodiments, the change in the absorption profile is measured by the disappearance peak of a peak between 350 and 380 nm, preferably 355-375 nm, or 360-365 nm pink in the presence of $Hg^{2+}$. In some embodiments, the change in the absorption profile is measured by the appearance peak of a peak between 550 and 600 nm, preferably 560-590 nm, or 570-580 nm in the presence of $Hg^{2+}$. In an embodiment, the change in absorbance is detected by eye as the composite changes from colorless to pink in the presence of $Hg^{2+}$.

In an embodiment, to monitor the fluorescence profile, the chemosensor is excited with light with a wavelength of 400-500 nm, preferably 420-480 nm, 440-460 nm, or approximately 450 nm. In some embodiments, the change in the fluorescence profile of the chemosensor is monitored between 500-650 nm, preferably 520-630 nm, 540-600 nm, 560-580 nm or approximately 570 nm. In some embodiments, the change in the fluorescence emission profile is measured by the appearance of a fluorescence band from 515-550 nm, preferably 520-540 nm, or approximately 530 nm. In an embodiment, the change in fluorescence is detected by eye following exposure of the aqueous solution with the chemosensor to an excitation light source. In an embodiment, the change in the absorption and/or fluorescence profile can be attributed to ring opening of the spirolactam ring of the FH following coordination of the $Hg^{2+}$ to the hydrazide group.

At step 106, the method 100 includes quantifying the change in the absorption and/or fluorescence profile to determine a concentration of $Hg^{2+}$ ions in the aqueous solution. In an embodiment, the composite has a binding constant of $10^5$-$10^6$ $M^{-1}$ towards the $Hg^{2+}$ ions. The high binding constant indicates a strong affinity (great attractive forces) between the $Hg^{2+}$ ions and the composite. In an embodiment, the FH in the composite and $Hg^{2+}$ ions form a 1:1 complex. In another embodiment, the MOF chemosensor composite is selective for detecting $Hg^{2+}$ ions. In another embodiment, the aqueous solution further comprises at least one metal cation selected from the group consisting of $Na^+$, $K^+$, $Ca^{2+}$, $Mg^{2+}$, $Ba^{2+}$, and $Ag^+$. In an embodiment, the metal ions in the aqueous solution may be $Li^+$, $Na^+$, $K^+$, $Be^{2+}$, $Mn^{2+}$, $Fe^{2+}$, $Co^{2+}$, $Ni^{2+}$, $Cu^{2+}$, $Zn^{2+}$, $Cd^{2+}$, $Sc^{3+}$, $Ti^{3+}$, $V^{3+}$, $Cr^{3+}$, $Fe^{3+}$, $Rh^{3+}$, $Ga^{3+}$, $In^{3+}$, $Ce^{4+}$, $Th^{4+}$, $Pa^{4+}$, $U^{4+}$, $Np^{4+}$, $Pu^{4+}$, $Mg^{2+}$, $Ca^{2+}$, $Sr^{2+}$, $Ba^{2+}$, $Al^{3+}$, $Y^{3+}$, $La^{3+}$, $Ag^+$, $Tl^+$, $Pb^{2+}$, $Ti^{3+}$, $Bi^{3+}$, $Sn^{2+}$, $Sn^{2+}$, or $Pd^{2+}$. In an embodiment, the change in the fluorescence emission profile occurs only in the presence of $Hg^{2+}$. In some embodiments, the limit of detection for $Hg^{2+}$ ions is 1-10 parts per billion (ppb), preferably 3-7 ppb or approximately 5 ppb.

In an embodiment, the method further includes adding ethylenediaminetetraacetic acid (EDTA) to the mixture to form a solution. The solution is then filtered and dried at a temperature of 80-120° C., preferably 90-110° C., or approximately 100° C. for at least one hour, preferably 1-3 hours, or approximately 2 hours, to form a recovered MOF chemosensor composite. In an embodiment, the EDTA removes $Hg^{2+}$ bound to the FH, and reforms the structure of the composite. In an embodiment, the recovered composite can then be introduced back into step 102 of the method 100. In an embodiment, there is no change in the absorption and/or fluorescence profile of the composite after up to 10 cycles of recovery. In an embodiment, the recovered MOF chemosensor composite maintains at least 90%, preferably 95%, or 100%, of the crystallinity of the MOF chemosensor composite.

EXAMPLES

The following examples describe and demonstrate exemplary embodiments of a fluorescein hydrazide-appended metal-organic framework for detecting mercury ions as described herein. The examples are provided solely for illustration and are not to be construed as limitations of the present disclosure, as many variations thereof are possible without departing from the spirit and scope of the present disclosure.

Experimental

Materials and General Methods

Trimesic acid (BTC) (95%), nickel nitrate hexahydrate (99.9% purity), fluorescein (99.9% purity), N,N dimethylformamide (DMF; 99.8% purity), ethanol (99.9% purity), dichloromethane (99.8% extra dry grade), and all other nitrates or chlorides of the metal salts were purchased from Sigma Aldrich Corporation, USA. NMR solvents: dimethyl sulfoxide-d6 (DMSO-d6; 99.9% purity) was purchased from Cambridge Isotope. All chemicals were used without further purification. The water used in this work was double distilled and filtered through a Millipore membrane. The solutions of metal ions were prepared from their nitrate and chloride salts, and anions were prepared from their sodium and potassium salts (analytical grade), followed by subsequent dilution to prepare the working solutions.

Instrumentation

Powdered X-ray diffraction patterns of the samples were recorded using a Rigaku MiniFlex diffractometer equipped with Cu-K radiation. The data were acquired over the 2θ range of 5° and 30°. The FTIR spectra of FH@Ni(MOF) were obtained using a Nicolet 6700 Thermo Scientific, USA instrument in the range of 400-4000 $cm^{-1}$ using KBr. Thermogravimetric analysis (TGA) of the samples was performed using a TA Q500, USA. An activated sample of FH@Ni(MOF) (10 mg) was heated in an alumina pan under airflow (60 mL $min^{-1}$) with a gradient of 10° C. $min^{-1}$ in the temperature range of 30-800° C. The $N_2$ adsorption isotherm of the MOFs for the BET surface area was calculated using a Micromeritics ASAP 2020 instrument, USA. The surface morphology of these materials was discerned using a field emission-scanning electron microscope (FESEM, LYRA 3 Dual Beam, Tescan, USA), which operated at 30 kV. The FESEM samples were prepared from suspension in ethanol. The absorption spectra of the MOF were studied using a Jasco V-670 spectrophotometer. Fluorescence spectra were measured using a Jasco Spectrophotometer FP-8500, Japan, equipped with a xenon discharge lamp and 1 cm quartz cells with a slit width of 2 nm for the source and the detector. Quantum yield studies were carried out using a Fluoromax-4 equipped with a Quanta-Phi integration sphere (Horiba), using a liquid sample holder at room temperature.

Example 1: Sample Preparation for Photophysical Studies

In a typical luminescence-sensing experimental setup, 1.0 mg of FH@Ni(MOF) powder was dispersed in 1 mL of water. A volume of 3 mL of a dispersed aqueous solution of FH@Ni(MOF) was placed in a 1 cm quartz cuvette. The absorption and emission responses were measured in situ after the incremental addition of freshly prepared analyte solutions. The mixtures were sonicated for 5 min after each incremental addition of the analytes for uniform dispersion during the luminescent measurements. All of the measurements were performed at 298 K.

Example 2: Practical Application in Water Samples

FH@Ni(MOF) was used to detect $Hg^{2+}$ in tap water, drinking water, and groundwater via the standard addition method. The water samples were filtered three times through a 0.2 mm membrane filter. Then, these three water samples were spiked with 10 and 15 µM of $Hg^{2+}$ and titrated against the FH@Ni(MOF).

Example 3: Synthesis of Fluorescein Hydrazide (FH)

Figure 2:
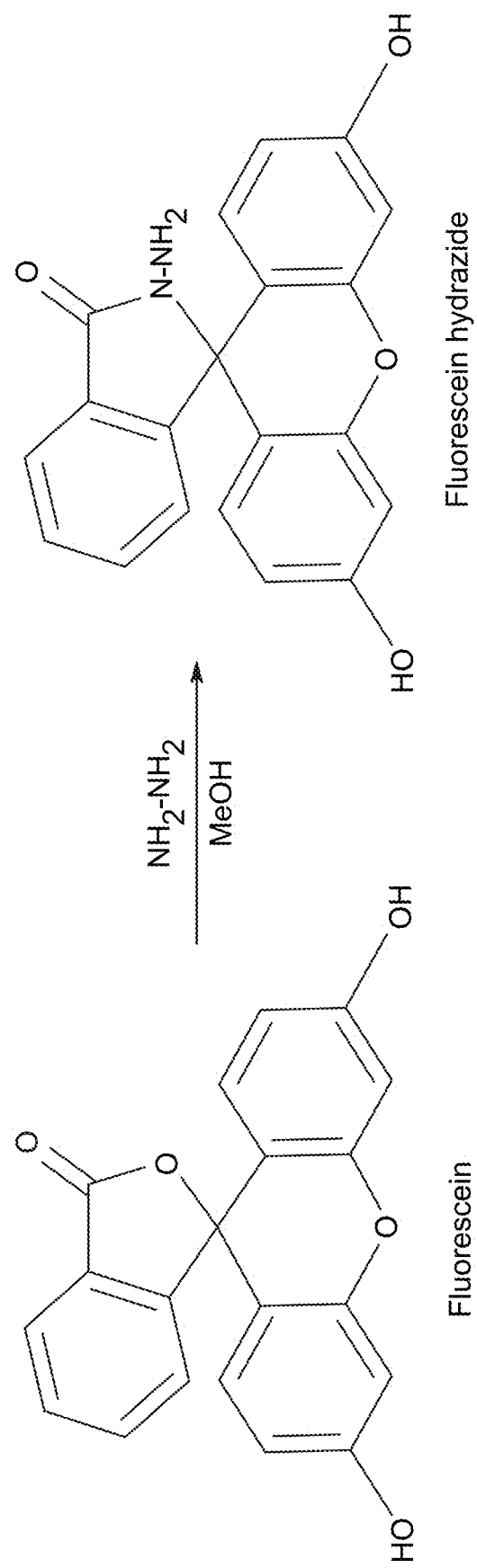
FIG. 2 illustrates the synthesis of fluorescein hydrazide (FH) according to certain embodiments.

Fluorescein (500 mg, 1.44 mmol) was dissolved in 20 mL methanol, and to it was added an excess amount of hydrazine hydrate (0.25 mL, 5.05 mmol). The reaction mixture was refluxed for 4 h and then cooled to room temperature, poured into distilled water, and extracted with ethyl acetate (6×25 mL). The combined extract was washed with brine, dried with anhydrous sodium sulfate, filtered, and then concentrated under a reduced pressure to yield (71%) FH. (FIG. 2)

Figure 3:
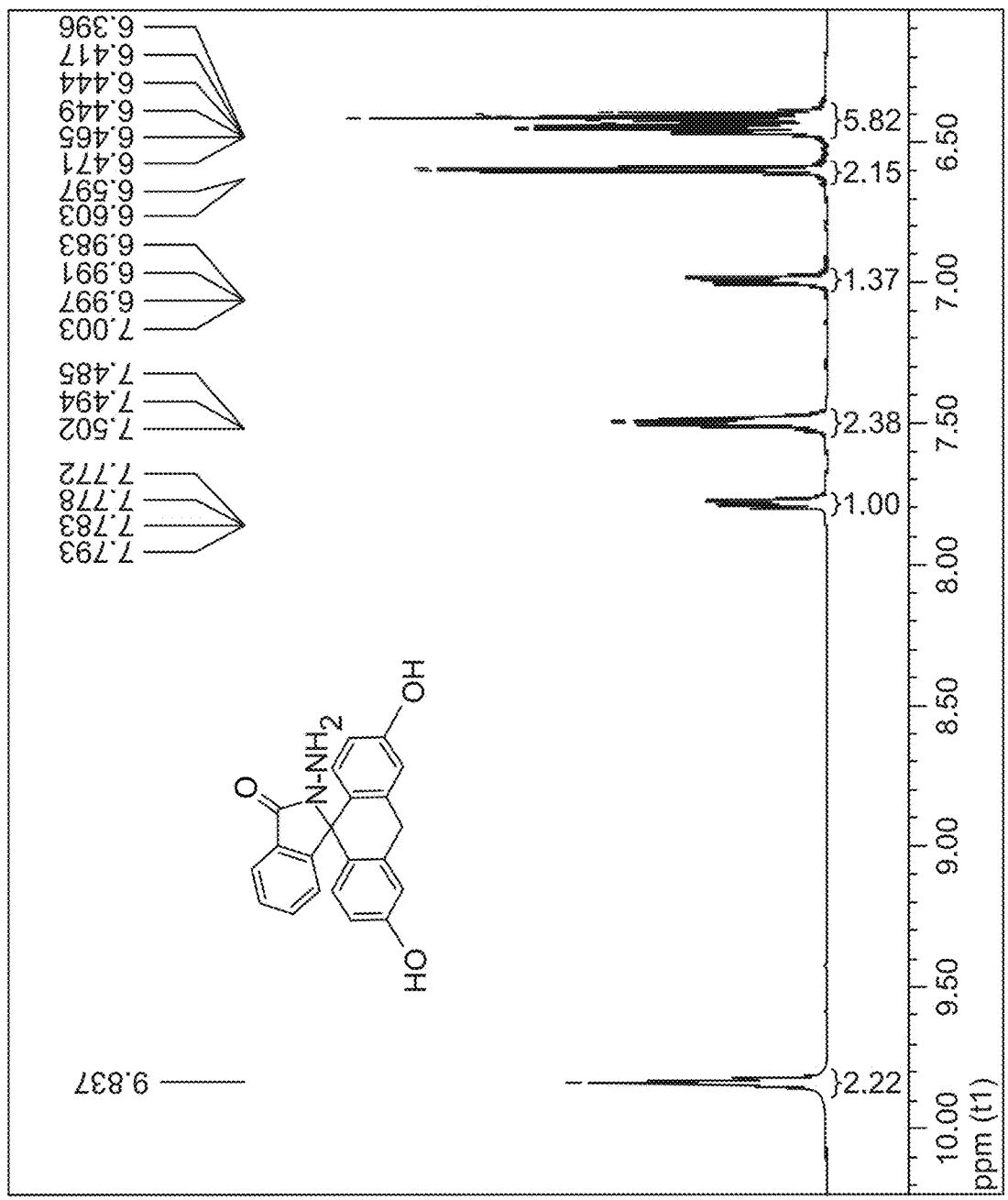
FIG. 3 shows $^1H$ NMR spectrum of FH in DMSO-d6 solution at 400 MHz, according to certain embodiments.

$^1$H NMR (400 MHz, DMSO-d6), d (ppm): 6.47-6.39 (m, 4H), 6.60 (d, J=3.0 Hz, 2H), 7.00-6.98 (m, 1H), 7.49 (t, J=4.0 Hz, 2H), 7.79-7.77 (m, 1H), 9.84 (s, 2H). (FIG. 3)

Figure 4:
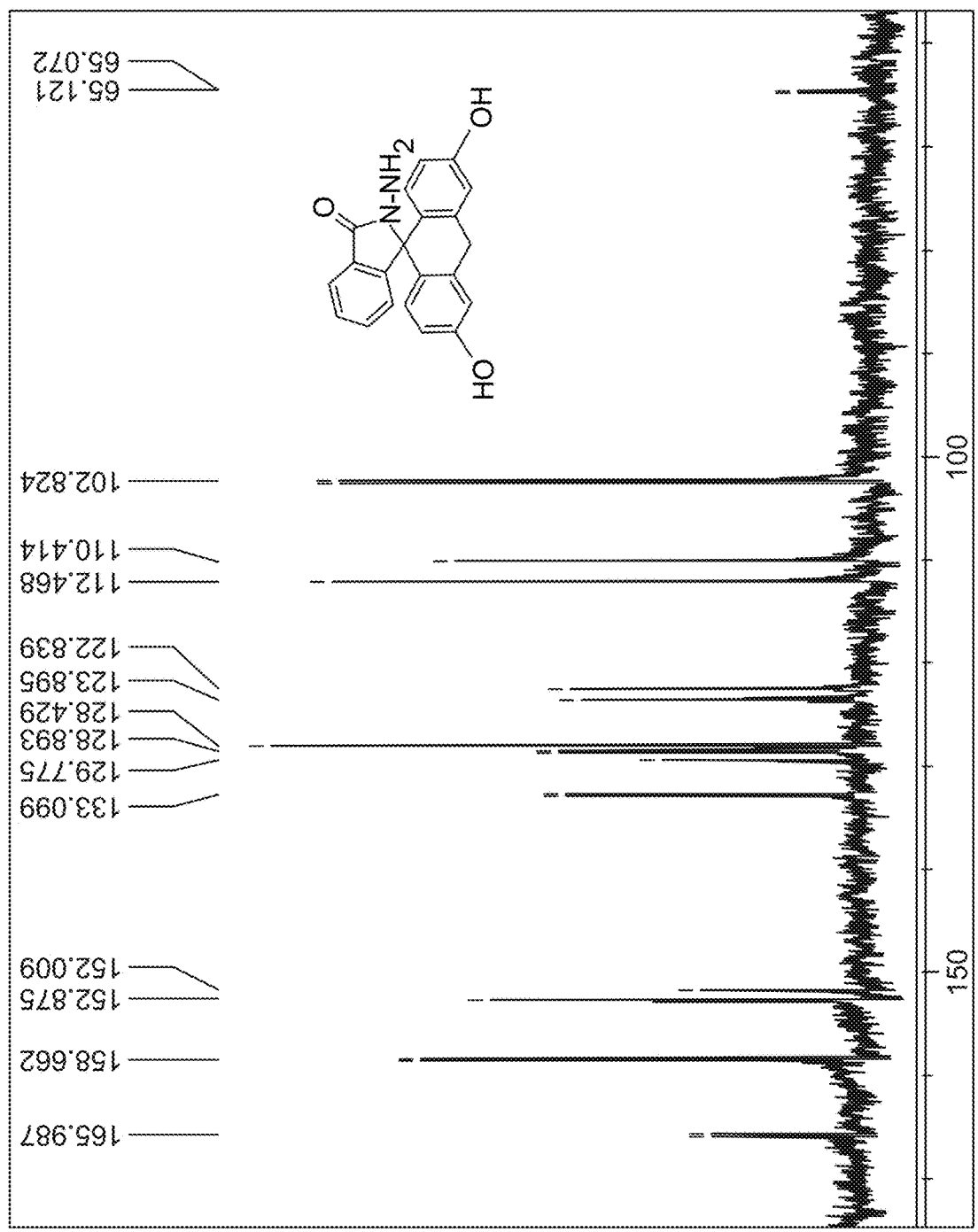
FIG. 4 shows $^{13}C$ NMR spectrum of FH in DMSO-d6 solution at 200 MHz, according to certain embodiments.

$^{13}$C NMR (100 MHz, DMSO-d6), d (ppm): 65.12, 102.82, 110.43, 112.48, 122.84, 123.89, 128.43, 128.89, 129.78, 133.10, 152.00, 152.88, 158.66, 165.99 (FIG. 4).

Example 4: Synthesis of Ni(MOF)

The Ni(MOF) [Ni$_3$(BTC)$_2$(H$_2$O)$_3$]·(DMF)$_3$(H$_2$O)$_3$ was prepared by the same method as that reported in the literature. Ni-MOF was synthesized by dissolving Ni(NO$_3$)$_2$. 6H$_2$O (291 mg, 1.0 mmol), and trimesic acid (BTC) (210 mg, 1.0 mmol) in DMF (20 mL) with ultrasonic vibration for 15 minutes. Further, 5 mL of acetic acid was added to the resultant mixture. The mixture was transferred to a 40 mL Parr steel autoclave and heated at 448 K for 72 h. Then, the autoclave was cooled in the air to room temperature. The resulting green icosahedral-shaped crystals were collected and washed with 3×10 mL of DMF for 3 days and 3×10 mL of CH$_2$Cl$_2$ for 3 days, yielding the required Ni-MOF in a 35% yield (related to the nickel salt).

Example 5: Synthesis of FH@Ni(MOF)

The Ni(MOF) was activated by heating the MOF at 150° C. in a vacuum oven for 6 h. The activated MOF (100 mg) was then suspended in ethanol (10 mL) containing fluorescein hydrazide (FH) (200 mg, 0.55 mmol) and refluxed at 358 K for 48 h. Then, the vial was cooled in the air to room temperature. The resulting FH@Ni(MOF) was washed three times with DMF (5-10 mL) using a centrifuge (10,000 rpm for 30 min) and then sequentially immersed in methanol (5-10 mL three times per day) for three 24 h periods. The washing with methanol was continued until the washing solution did not contain any residual dye, as confirmed by absorption studies of the methanol extracts obtained after washing. This justified that no dye was leaching from the FH@Ni(MOF) powder. Finally, FH@Ni(MOF) was dried by removing the solvent under vacuum for 24 h at 80° C.

FT-IR (KBr, cm$^{-1}$): 3415, 1680, 1629, 1579, 1499, 1439, 1378, 1185, 1111, 936, 836, 795, 754, 701.

Anal. Calcd. for C$_{144}$H$_{108}$N$_{12}$O$_{33}$Ni$_3$[Ni$_3$(BTC)$_2$(H$_2$O)$_3$]. (C$_{21}$H$_{16}$N$_2$O$_3$)$_6$: C, 63.81; H, 4.02; N, 6.20. Found: C, 62.78; H, 4.15; N, 6.37.

Example 6: Determination of the Rate Constant

The rate constant was calculated using the following equation (1).

$$\frac{F_0}{(F-F_o)} = \left[\frac{a}{b-a}\right]\left[\left(\frac{1}{Ks[M]}\right)+1\right] \quad (1)$$

where $F_o$ is the absorbance or fluorescence intensities of the free host (FH@Ni(MOF)), F is the absorbance or fluorescence intensities of the host-guest complex, a and b are constants, Ks is the rate constant, and M is the concentration of the guest ($Hg^{2+}$). When $F_o/(F-F_o)$ is plotted against the reciprocal of the concentration of the guest (hydrazine) $[M]^{-1}$, the rate constant is given by the ratio intercept/slope.

Example 6: Structural Characterization of FH@Ni(MOF)

Figure 5:
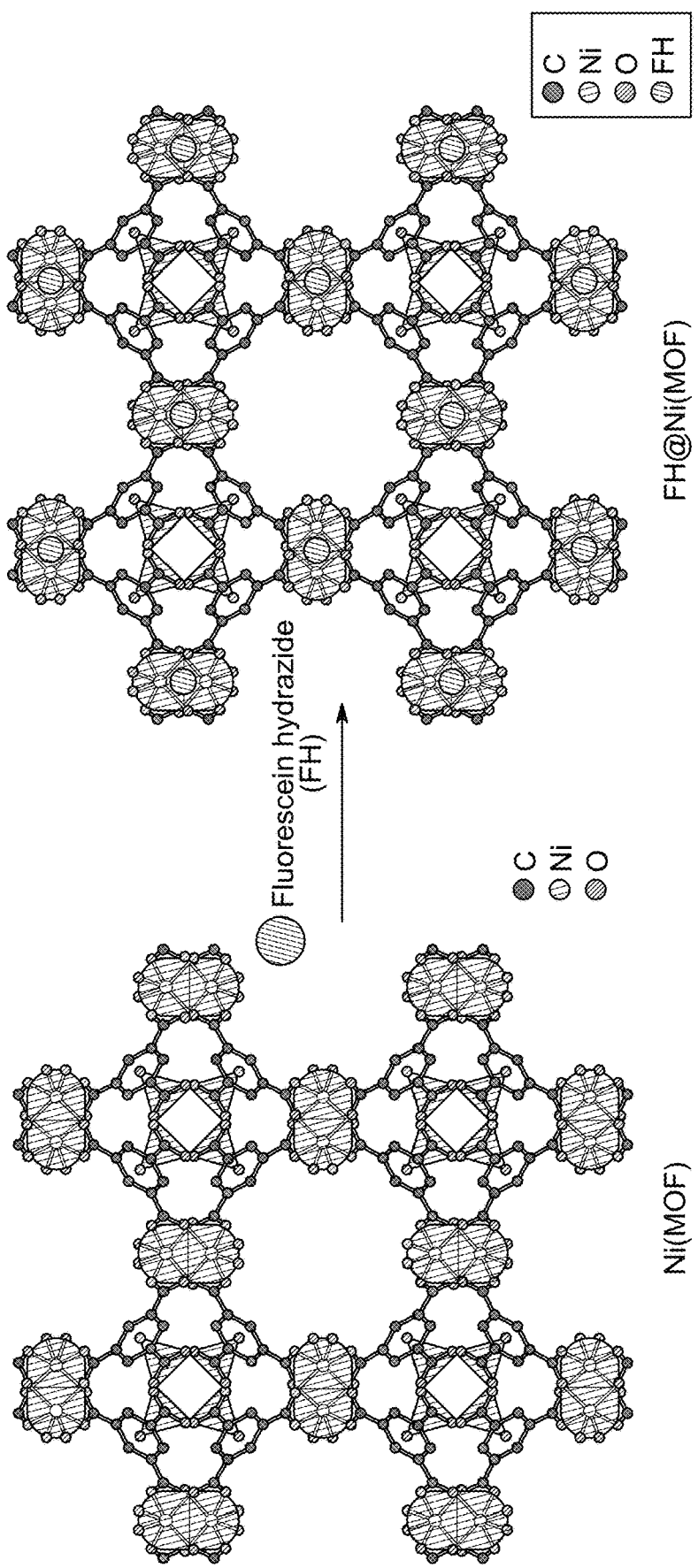
FIG. 5 shows the synthesis of FH@Ni(MOF) from Ni(MOF), according to certain embodiments.

The FH was synthesized using the methods given in the literature and characterized by the $^1$H and $^{13}$C NMR (FIGS. 2-4). The Ni(MOF) was prepared according to the method followed in the literature. The Ni(MOF) was further activated by evacuation at a high temperature to de-coordinate the aqua ligands from the nickel clusters and generate coordinately unsaturated sites (CUS). Upon interaction with the FH, the CUS are coordinately occupied with the lone pair electrons of the nitrogen in the FH to give the composite FH@Ni(MOF) (FIG. 5).

Figure 6:
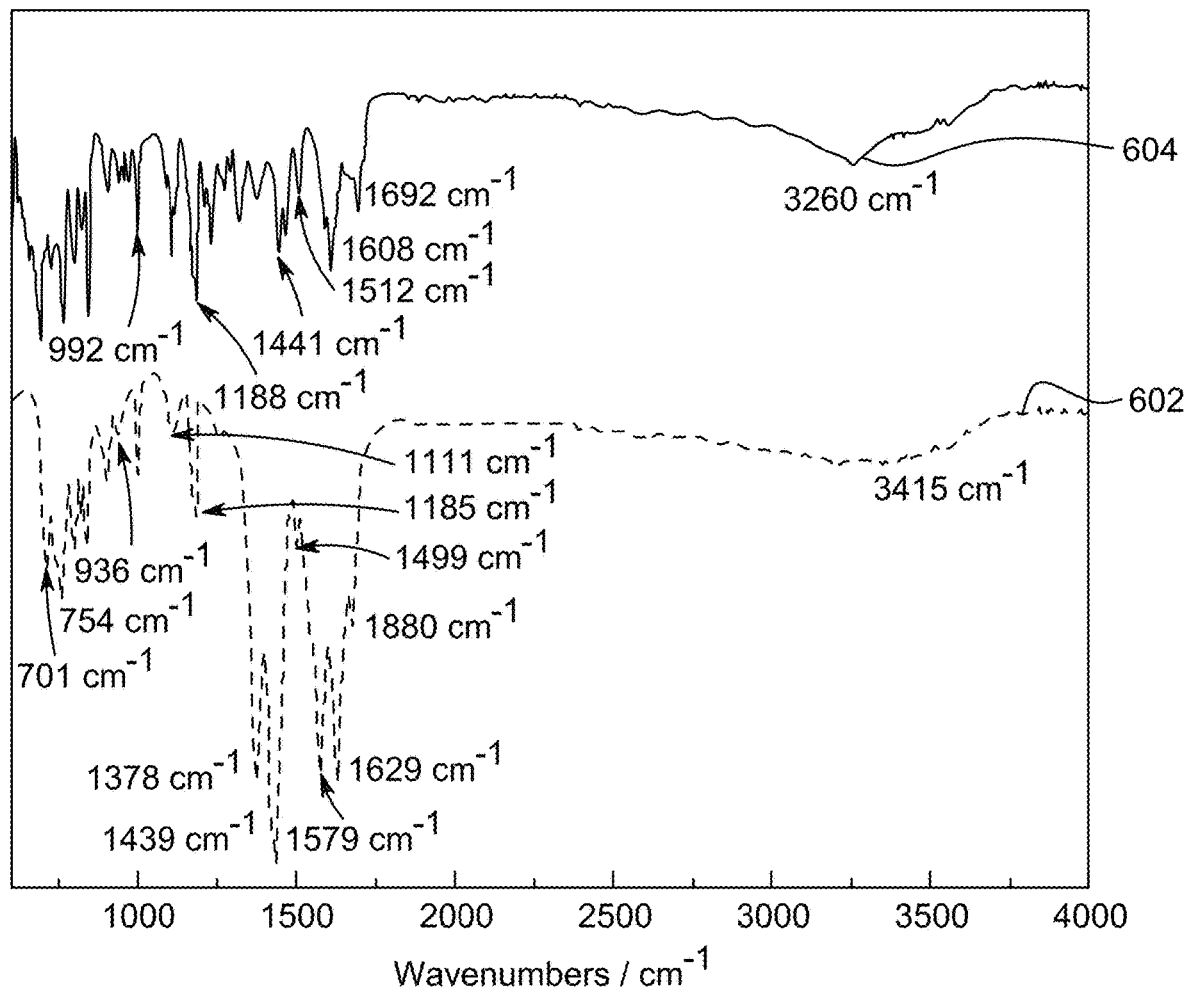
FIG. 6 shows Fourier Transform Infrared (FTIR) spectrum of FH and FH@Ni(MOF), according to certain embodiments.
Figure 7:
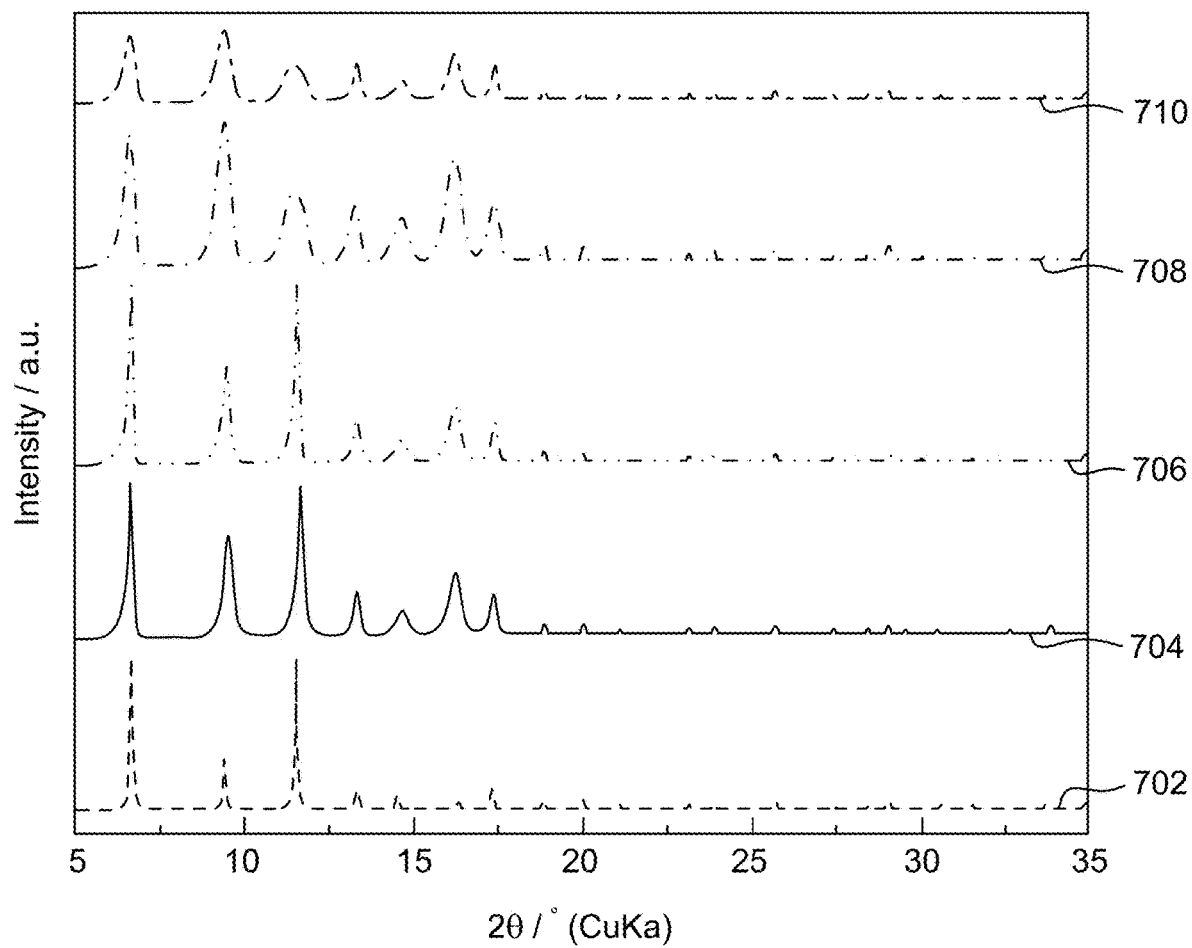
FIG. 7 shows powder X-ray diffraction (PXRD) spectra of simulated Ni(MOF), synthesized Ni(MOF), activated Ni(MOF), FH@NiMOF, and FH@Ni(MOF)+$Hg^{2+}$ ions, according to certain embodiments.

The structural characterization of the composite was carried out using FTIR and PXRD. The FTIR spectra of the FH@Ni(MOF) (602), and the FH (604) are depicted in FIG. 6. The bands at 701 cm$^{-1}$ and 754 cm$^{-1}$ correspond to the out-of-plane aromatic C—H bending modes of the benzene ring of the linker, while the band at 936 cm$^{-1}$ is due to the bending mode of the aromatic C—H of the fluorescein hydrazide. The band at 1111 cm$^{-1}$ is designated to the C—H in-plane bending of the benzene ring, while the band at 1185 cm$^{-1}$ is assigned to the FH's N—N stretching. The symmetric and asymmetric stretching modes of the carbonyl moiety in the COO— group are represented by the strong bands at 1378 and 1439 cm$^{-1}$ and 1579 and 1629 cm$^{-1}$, respectively. The bands at 1499 cm$^{-1}$ and 1680 cm$^{-1}$ are likely due to the in-plane bending of the H—N—N and C=O stretching of the FH, respectively. The small band at 3415 cm$^{-1}$ corresponds to the O—H stretching vibration of the FH. The simultaneous presence of both the IR bands from the Ni(MOF) and FH in FH@Ni(MOF) illustrates the formation of the composite. The PXRD for the samples of simulated Ni(MOF) (702), as-synthesized Ni(MOF) (704), activated Ni(MOF) (706), FH@Ni(MOF) (708), and FH@Ni(MOF) bonded to $Hg^{2+}$ (710) are depicted in the FIG. 7. PXRD confirmed the consistency in the crystallinity and phase purity was well retained in the as-synthesized Ni(MOF) (704), activated Ni(MOF) (706), and FH@Ni (MOF) (708), respectively (FIG. 7).

Figure 8:
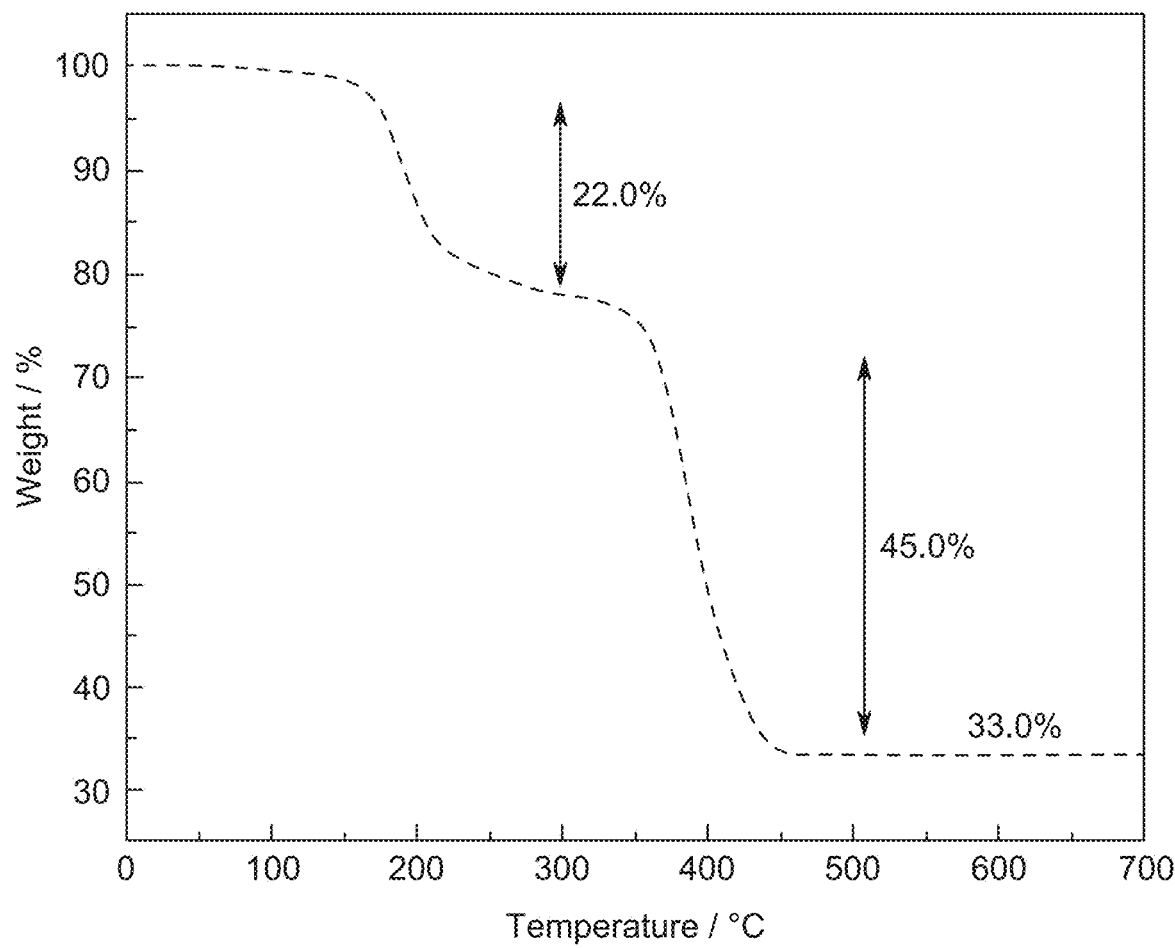
FIG. 8 shows a thermogravimetric analysis (TGA) of FH@NiMOF, according to certain embodiments.

Further, TGA of the composite FH@Ni(MOF) was carried out to understand the thermal stability of the composite. The results of this study are depicted in FIG. 8. From FIG. 8, it can be observed that weight loss occurred in two stages: (a) In the first step, there was a weight loss of 22.0% at 150° C., which corresponds to the decomposition of the FH. (b) The second step showed a sudden weight loss of about 45.0% at 375-450° C. due to the thermal disintegration of the framework. The final silt of 33.0% can be ascribed to the nickel oxide formed after decomposition.

Figure 9:
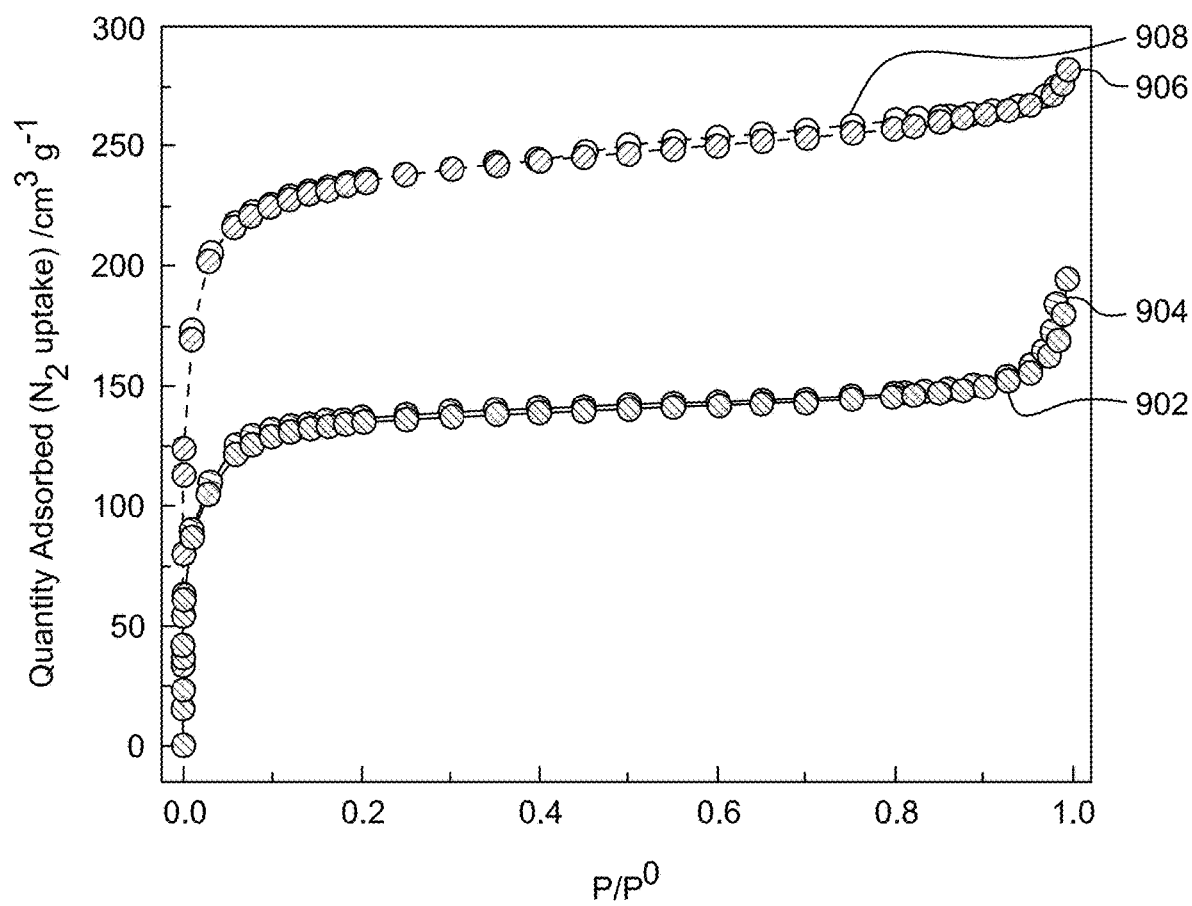
FIG. 9 shows a $N_2$ adsorption isotherm of Ni(MOF) and FH@NiMOF, according to certain embodiments.

The $N_2$ adsorption-desorption isotherm of Ni(MOF) (906 and 908) and FH@NiMOF (902 and 904) are depicted in FIG. 9. The FH@Ni(MOF) indicates that it is microporous, with a characteristic Type I isotherm. The Brunauer-Emmett-Teller (BET) surface area for the FH@Ni(MOF) was calculated to be 380 $m^2/g$. The surface area of FH@Ni (MOF) was much decreased compared to the pristine Ni(MOF) due to the presence of the FH occupying the pores of the MOF.

Figure 10:
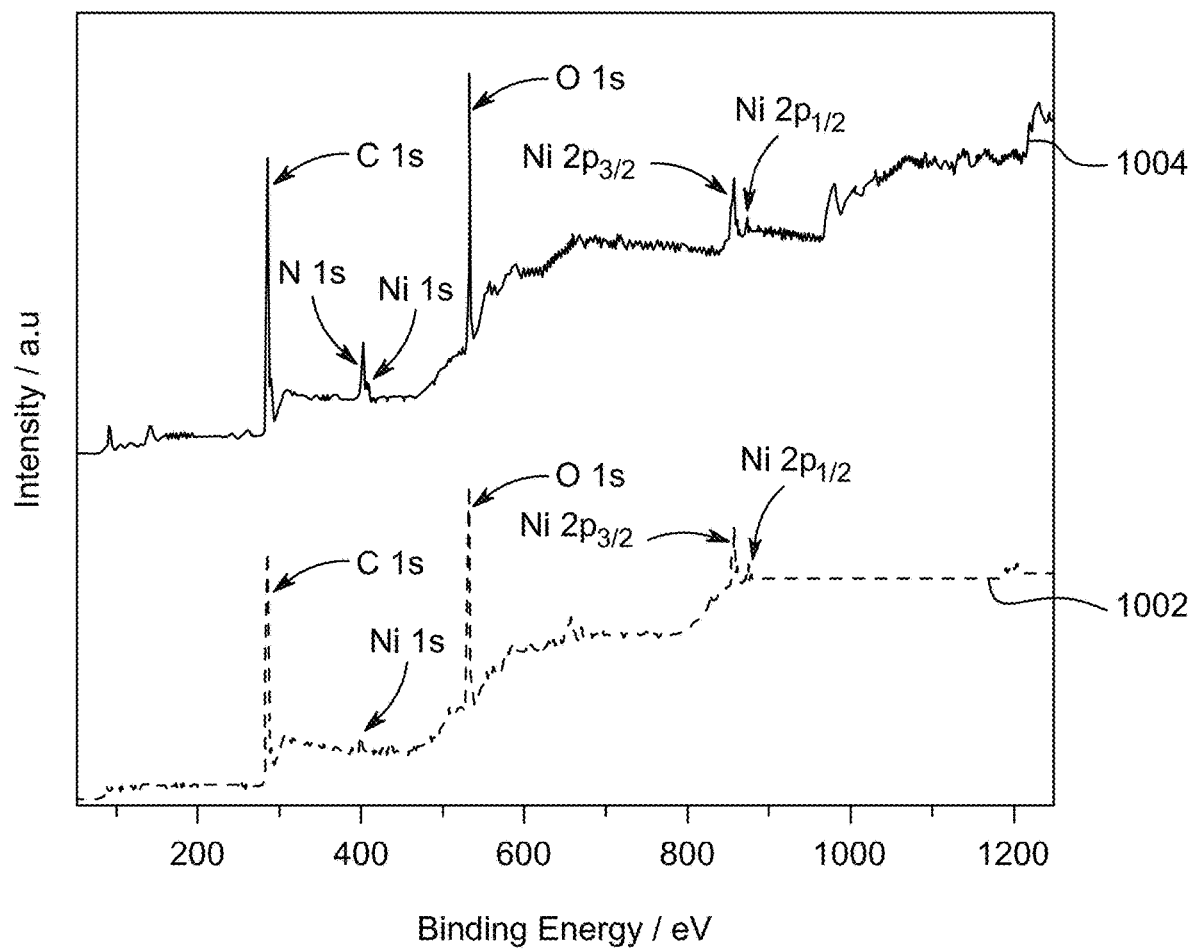
FIG. 10 shows X-ray photoelectron spectroscopy (XPS) of FH and FH@Ni(MOF), according to certain embodiments.
Figure 11:
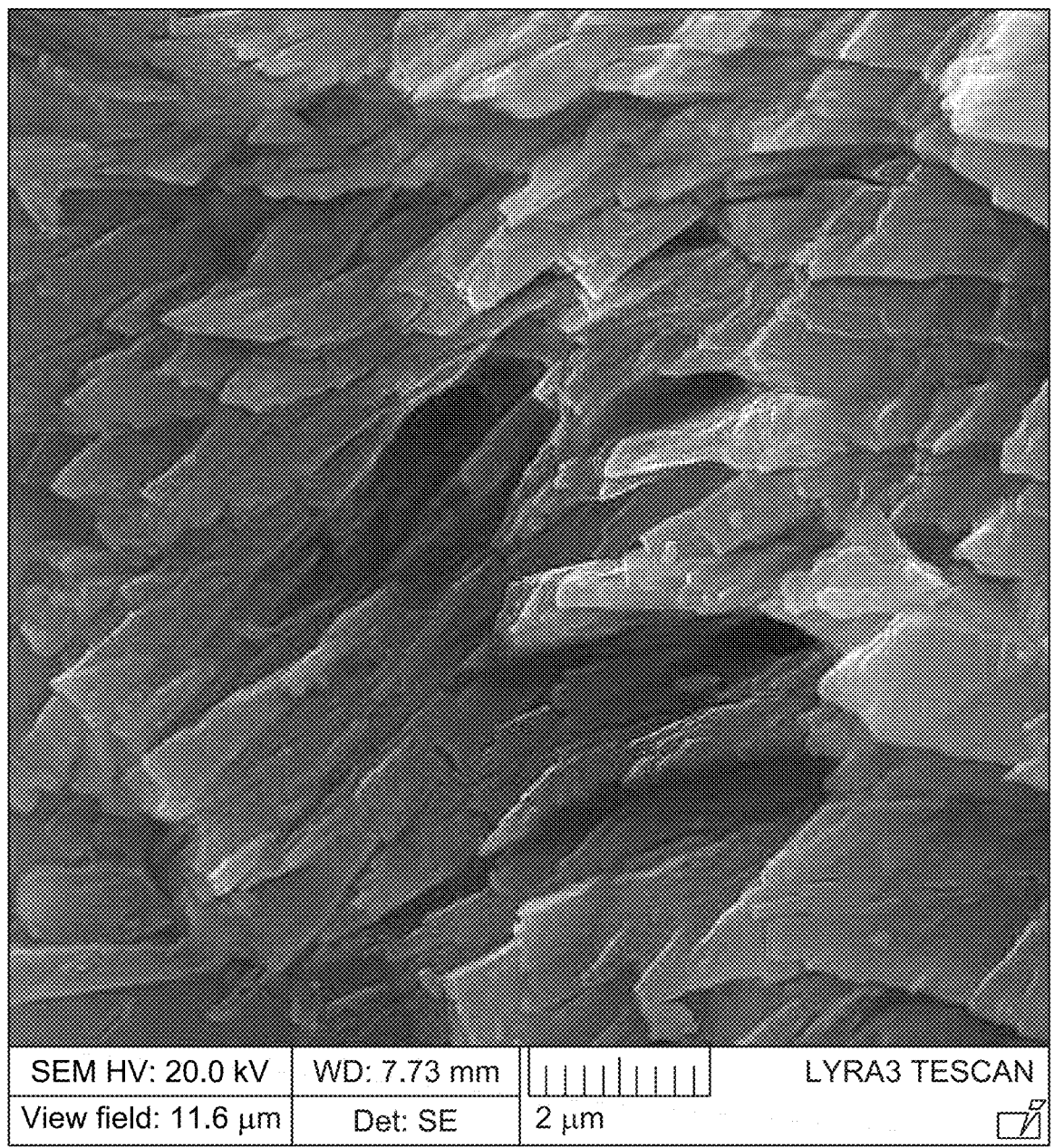
FIG. 11 shows a scanning electron microscope (SEM) image of FH@Ni(MOF), according to certain embodiments.

The XPS spectra of Ni(MOF) (1002) and FH@Ni(MOF) (1004) were recorded, and the results of this study are depicted in FIG. 10. Both the spectra had peaks at 856.1 eV and 873.3 eV, corresponding to Ni 2p3/2 and 2p1/2, indicating that nickel mainly exists as $Ni^{2+}$. The peak at 397.2 is also attributed to Ni 1 s. In both spectra, the peaks at 284.1 eV (C 1 s) and 531.9 eV (O 1 s) resemble the characteristic peaks for C, and O, respectively. These peak intensities are much higher than those for the pristine Ni(MOF), indicating the presence of FH. Furthermore, an additional peak at 401.6 eV in the case of FH@Ni(MOF) suggests the presence of N 1 s from the FH. The scanning electron microscopy (SEM) images of the microcrystalline composite FH@Ni(MOF) show a uniform morphology of rod-shaped structures assembled into sheets (FIG. 11). The amount of fluorescein hydrazide appended in the FH@Ni(MOF), as calculated by the alkaline digestion, was found to be approximately 0.211 g $g^{-1}$ (0.61 mmole·$g^{-1}$) of FH@Ni(MOF).

Example 7: Cation Sensing Properties of FH@Ni(MOF)

Figure 12:
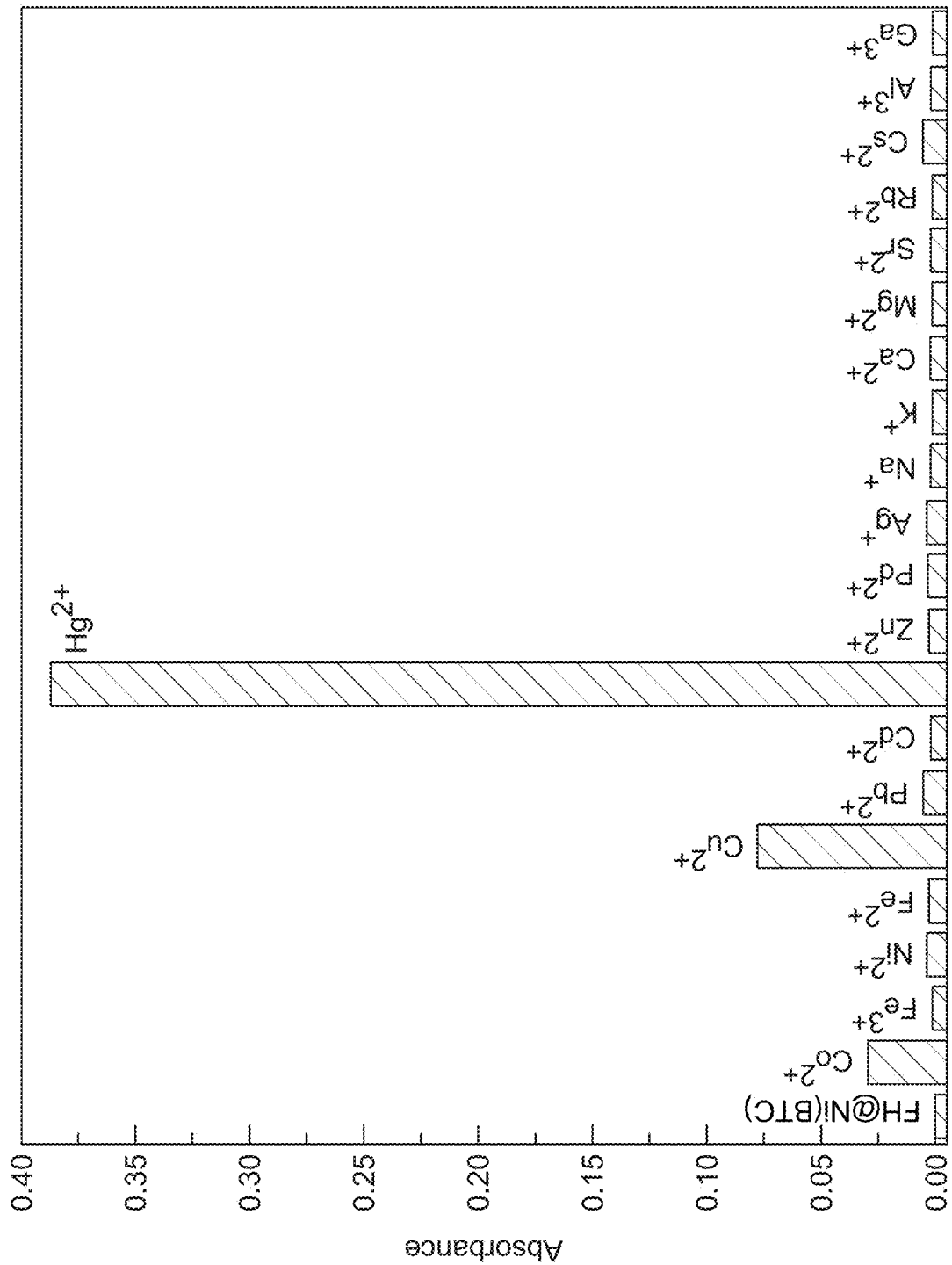
FIG. 12 shows a change in the UV-vis spectrum of FH@Ni(MOF) in water upon the addition of 200 µL of different metal cations ($10^{-2}$ M), according to certain embodiments.
Figure 13:
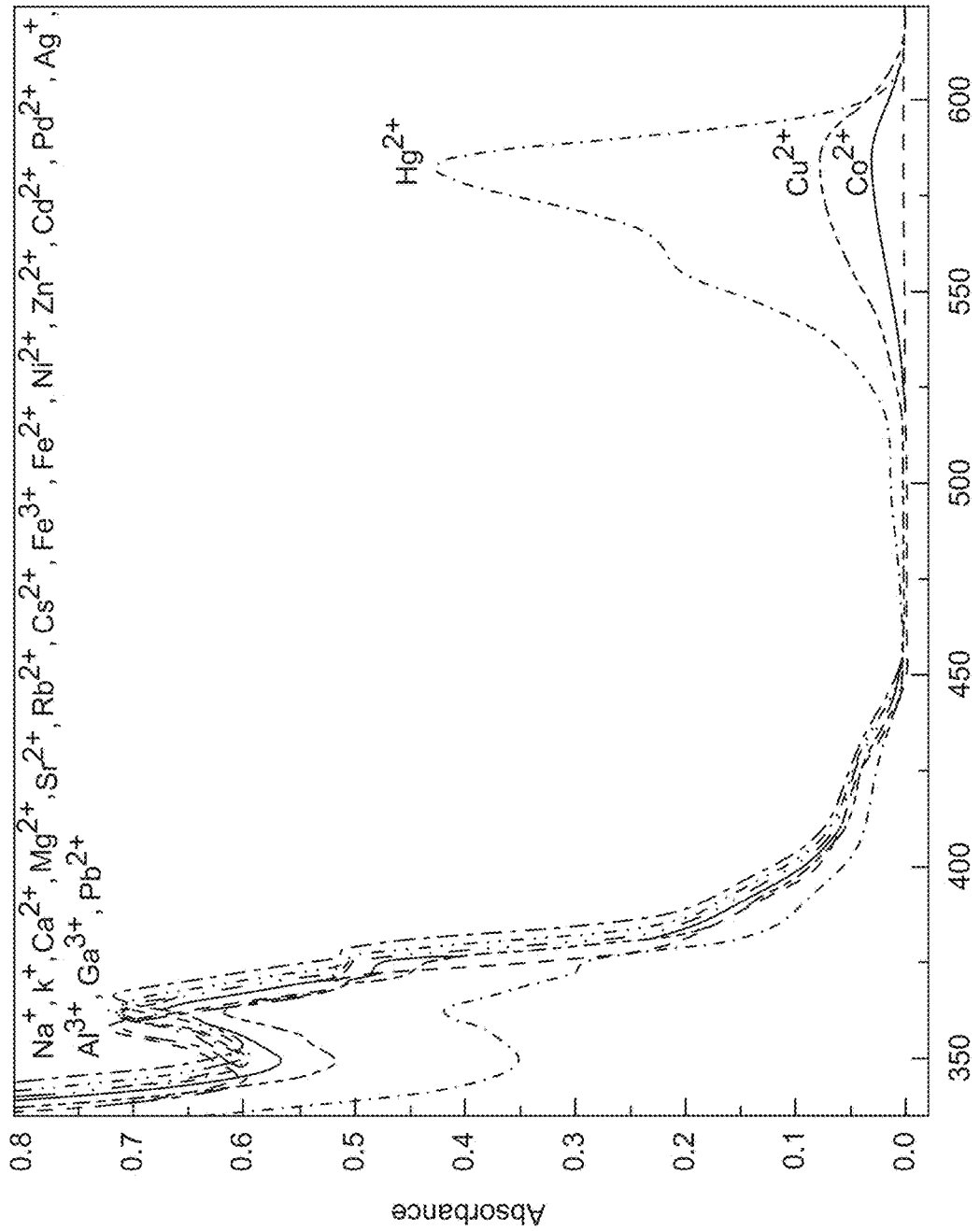
FIG. 13 shows a change in the UV-vis spectrum of FH@Ni(MOF) in water upon the addition of 200 µL of different metal cations ($10^{-2}$ M), according to certain embodiments.
Figure 14:
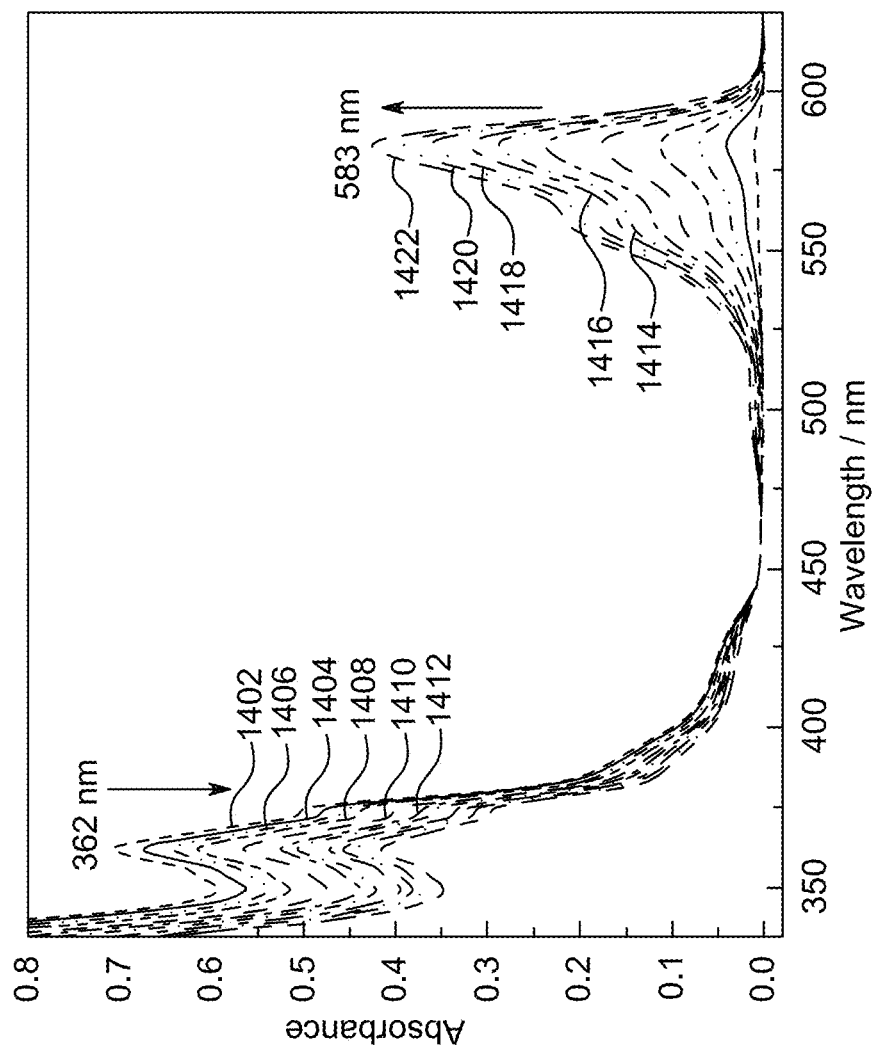
FIG. 14 depicts changes in UV-vis spectra of FH@Ni(MOF) with the incremental addition of $Hg^{2+}$ ($10^{-2}$ M) in water, according to certain embodiments.
Figure 15:
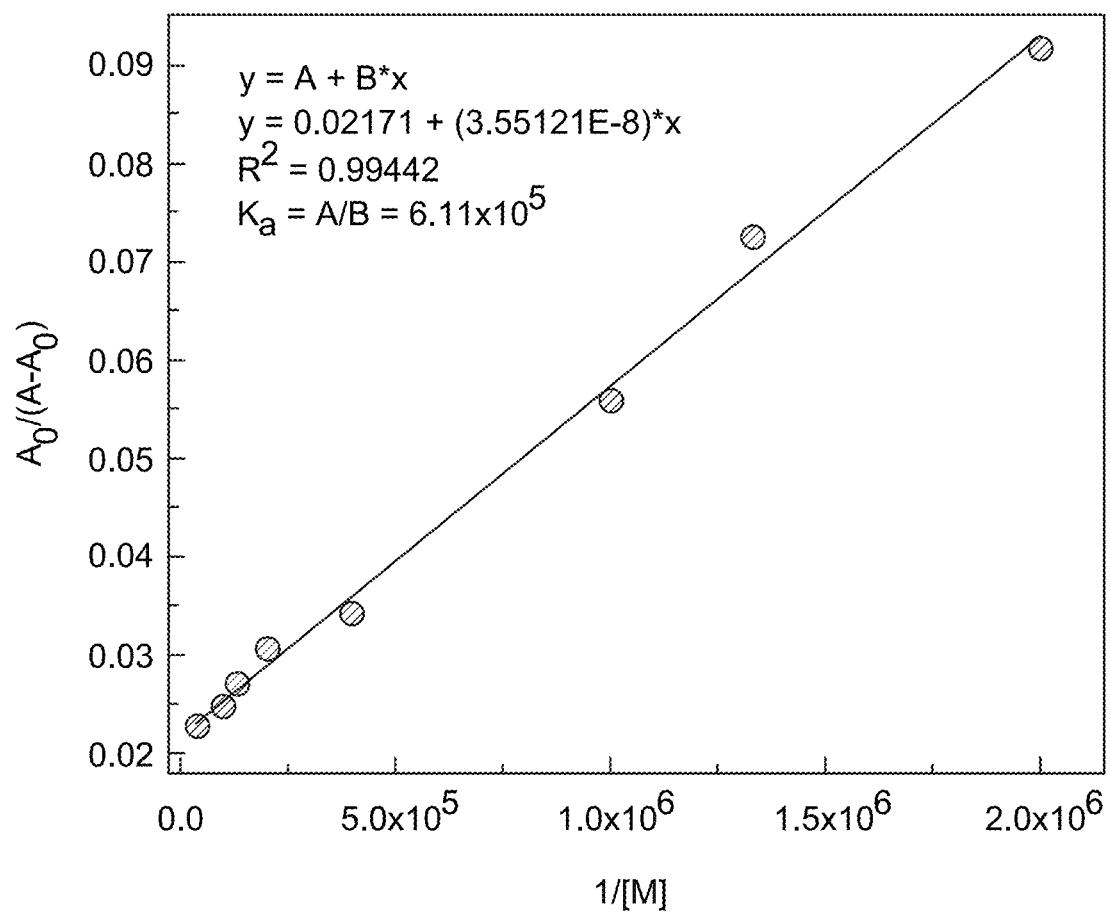
FIG. 15 shows a linear regression curve of FH@Ni(MOF) obtained by plotting absorbance $A_0/(A-A_0)$ as a function of $1/[Hg^{2+}]$ in an aqueous system, according to certain embodiments.
Figure 16:
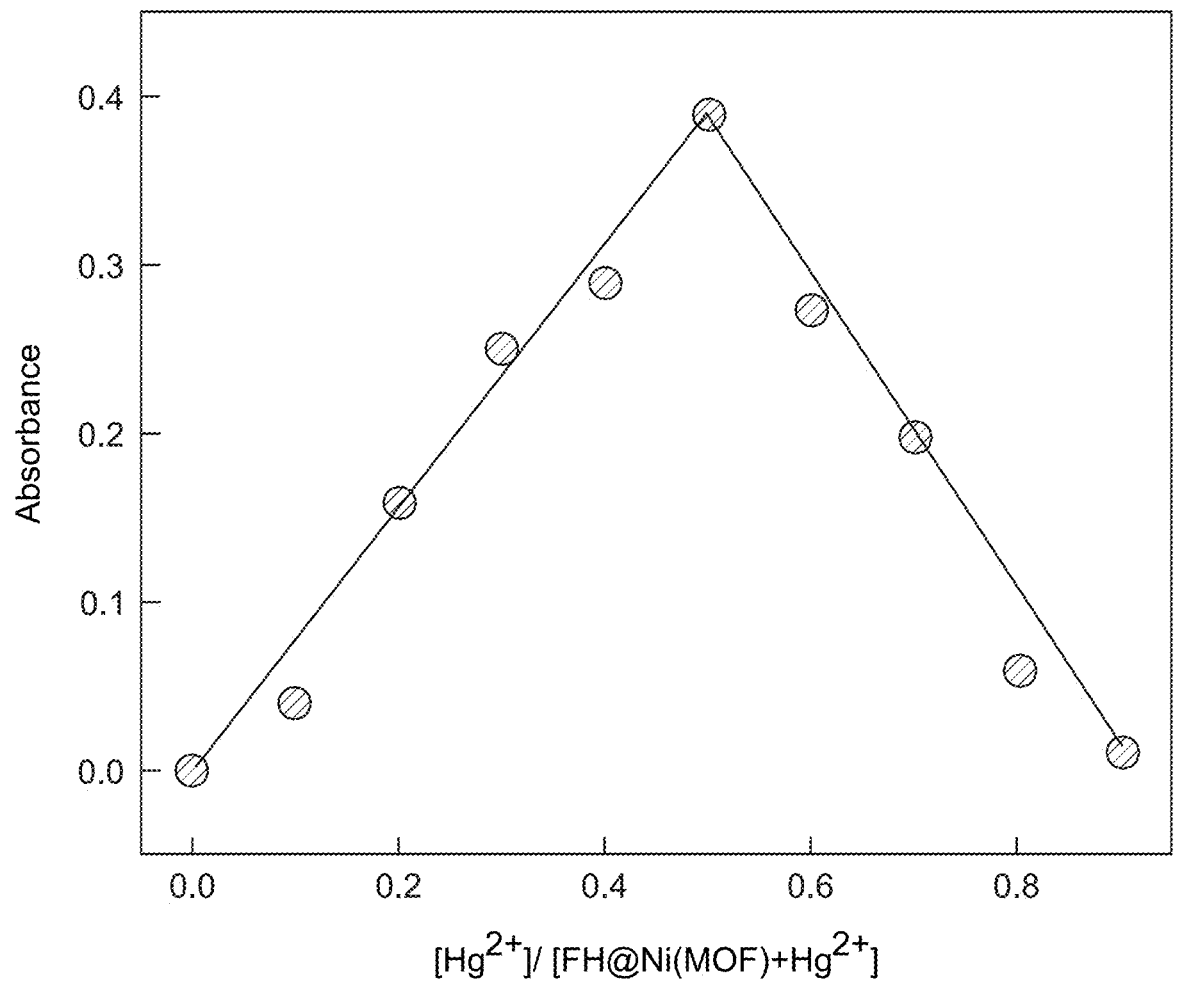
FIG. 16 shows a Job's plot for FH@Ni(MOF) with $Hg^{2+}$ in water, according to certain embodiments.

Ni(MOF) does not have effective optical or binding properties for heavy metals. Nevertheless, it produces both optical and selective binding properties with heavy metals to form a composite with the FH. Thus, the absorbance and emission studies of FH@Ni(MOF) were carried out in an aqueous solution such as an emulsion. The FH@Ni(MOF) has an absorption maximum at 362 nm due to the $\pi$-$\pi^*$ transition of the aromatic rings. Initial studies with different metal cations, namely, $Na^+$, $K^+$, $Ca^{2+}$, $Mg^{2+}$, $Sr^{2+}$, $Rb^{2+}$, $Cs^{2+}$, $Al^{3+}$, $Ga^{3+}$, $Fe^{2+}$, $Fe^{3+}$, $Cu^{2+}$, $Ni^{2+}$, $Pb^{2+}$, $Cd^{2+}$, $Co^{2+}$, $Zn^{2+}$, $Pd^{2+}$, and $Ag^+$, indicate that only the $Hg^{2+}$ ion decreases the absorbance at 362 nm and the appearance of a new absorption maximum at 583 nm (FIGS. 12 and 13). This peak is characteristic of the opening of the spirolactam ring and binding with the $Hg^{2+}$ (FIG. 4). This new absorption triggers the color change of the emulsion from colorless to pink, which is visible to the naked eye. The slow addition of $Hg^{2+}$ to the emulsion of FH@Ni(MOF) (1402) resulted in the new peak at 583 nm, with an asynchronous decrease in the absorbance band at 362 nm (FIG. 14). The study was performed where the concentration of mercury ions in the sample is in range of $1\times10^{-6}$ mol/L to $2.5\times10^{-4}$ mol/L, particularly, $1\times10^{-6}$ mol/L (1404), $2.5\times10^{-6}$ mol/L (1406), $5\times10^{-6}$ mol/L (1408), $7.5\times10^{-6}$ mol/L (1410), $1\times10^{-5}$ mol/L (1412), $2.5\times10^{-5}$ mol/L (1414), $5\times10^{-5}$ mol/L (1416), $7.5\times10^{-5}$ mol/L (1418), $1\times-4$ mol/L (1420), and $2.5\times10^{-4}$ mol/L (1422), respectively. It can also be observed that the intensity of the absorbance band at 583 nm increases with an increase in the concentration of $Hg^{2+}$ ions. From the UV-vis titration, the binding constant was calculated to be $6.1\times10^{-5}$ $M^{-1}$ (error estimated to be ≤10%) (FIG. 15). Moreover, Job's plot experiment of FH@Ni(MOF) with the $Hg^{2+}$ ion indicated the formation of a 1:1 complex between the FH of the FH@Ni(MOF) and the $Hg^{2+}$ ion (FIG. 16).

Figure 17:
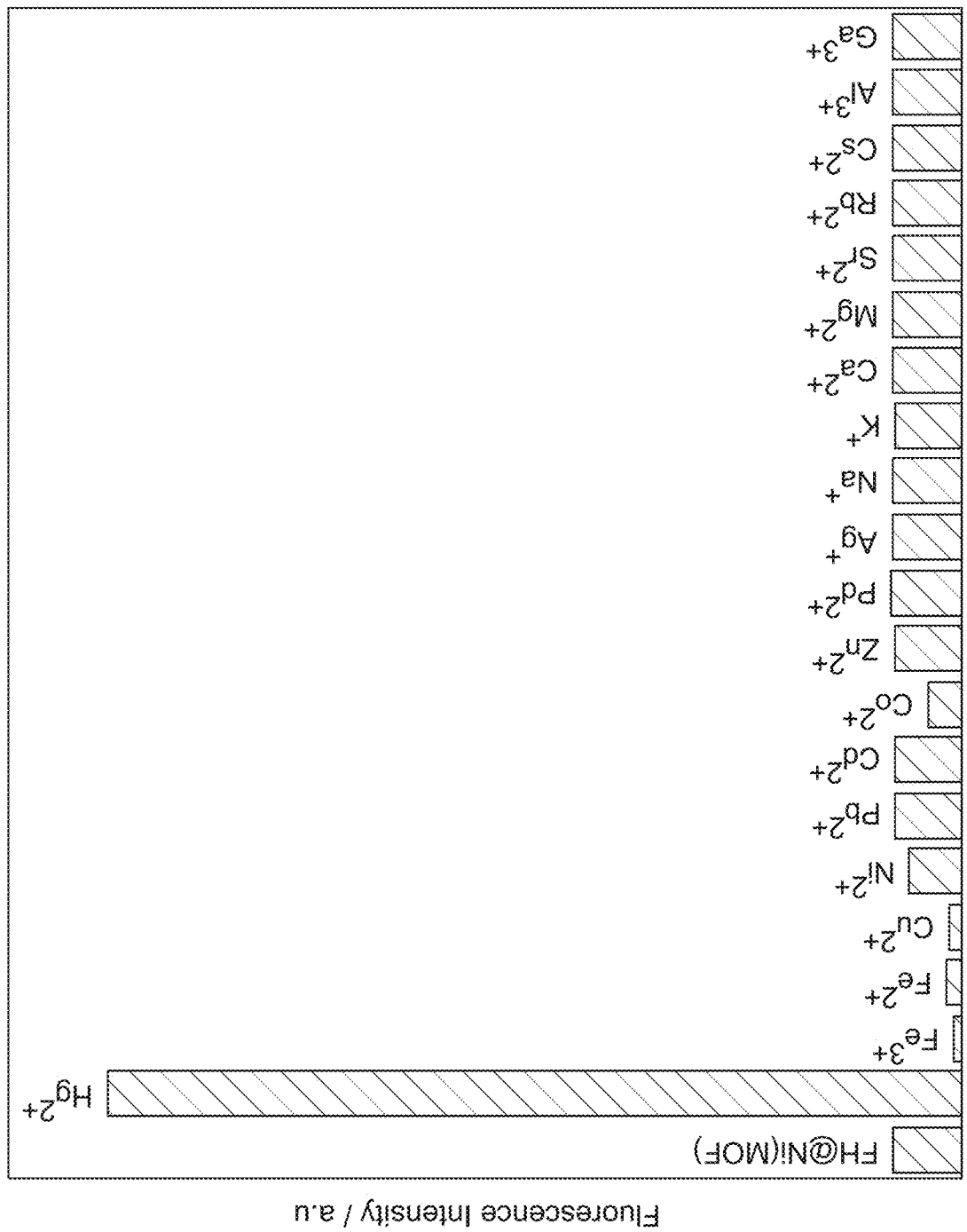
FIG. 17 depicts a change in fluorescence intensity of FH@Ni(MOF) in water upon the addition of 200 µL of different metal cations ($10^{-2}$ M), according to certain embodiments.
Figure 18:
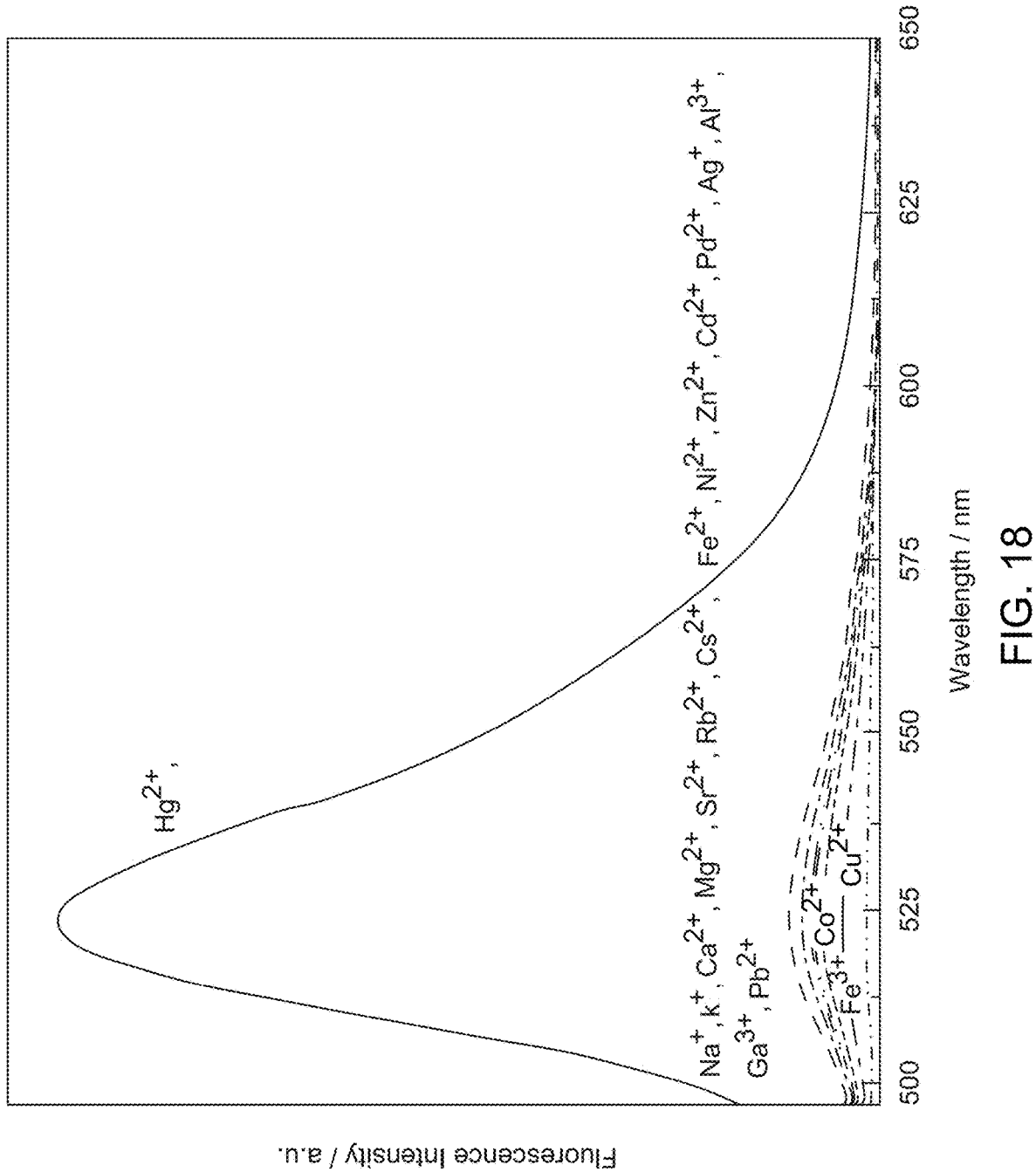
FIG. 18 depicts a change in fluorescence intensity of FH@Ni(MOF) in water upon the addition of 200 µL of different metal cations ($10^{-2}$ M), according to certain embodiments.

The emission properties of composite FH@Ni(MOF) were investigated in aqueous emulsion with different biologically and non-biologically relevant cations, particularly, $Na^+$, $K^+$, $Ca^{2+}$, $Mg^{2+}$, $Sr^{2+}$, $Rb^{2+}$, $Cs^{2+}$, $Al^{3+}$, $Ga^{3+}$, $Fe^{2+}$, $Fe^{3+}$, $Cu^{2+}$, $Ni^{2+}$, $Pb^{2+}$, $Cd^{2+}$, $Co^{2+}$, $Zn^{2+}$, $Pd^{2+}$, $Hg^{2+}$ and $Ag^+$. It was observed that only $Hg^{2+}$, in addition to the composite FH@Ni(MOF), produced an enhancement in the emission at 523 nm upon excitation at 460 nm (FIG. 17). None of the cations except $Hg^{2+}$ induced any noticeable enhancement in emission when interacting with any metal ions. However, transition metal ions $Cu^{2+}$, $Co^{2+}$, and $Fe^{3+}$ induced complete or partial quenching on binding with the chemosensor due to their paramagnetic nature (FIG. 18).

Figure 19:
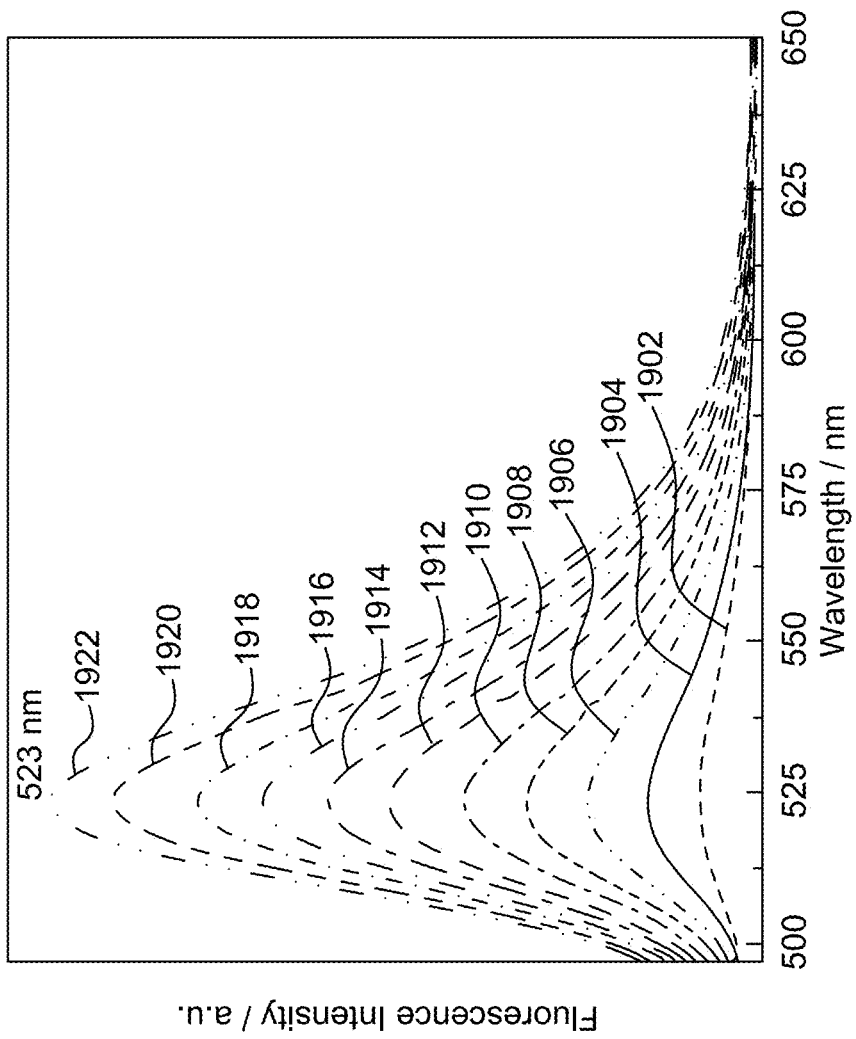
FIG. 19 is a plot depicting changes in fluorescence emission spectra of FH@Ni(MOF) with the incremental addition of $Hg^{2+}$ ($10^{-2}$ M) in water ($\lambda_{ex}$=460 nm), according to certain embodiments.
Figure 20:
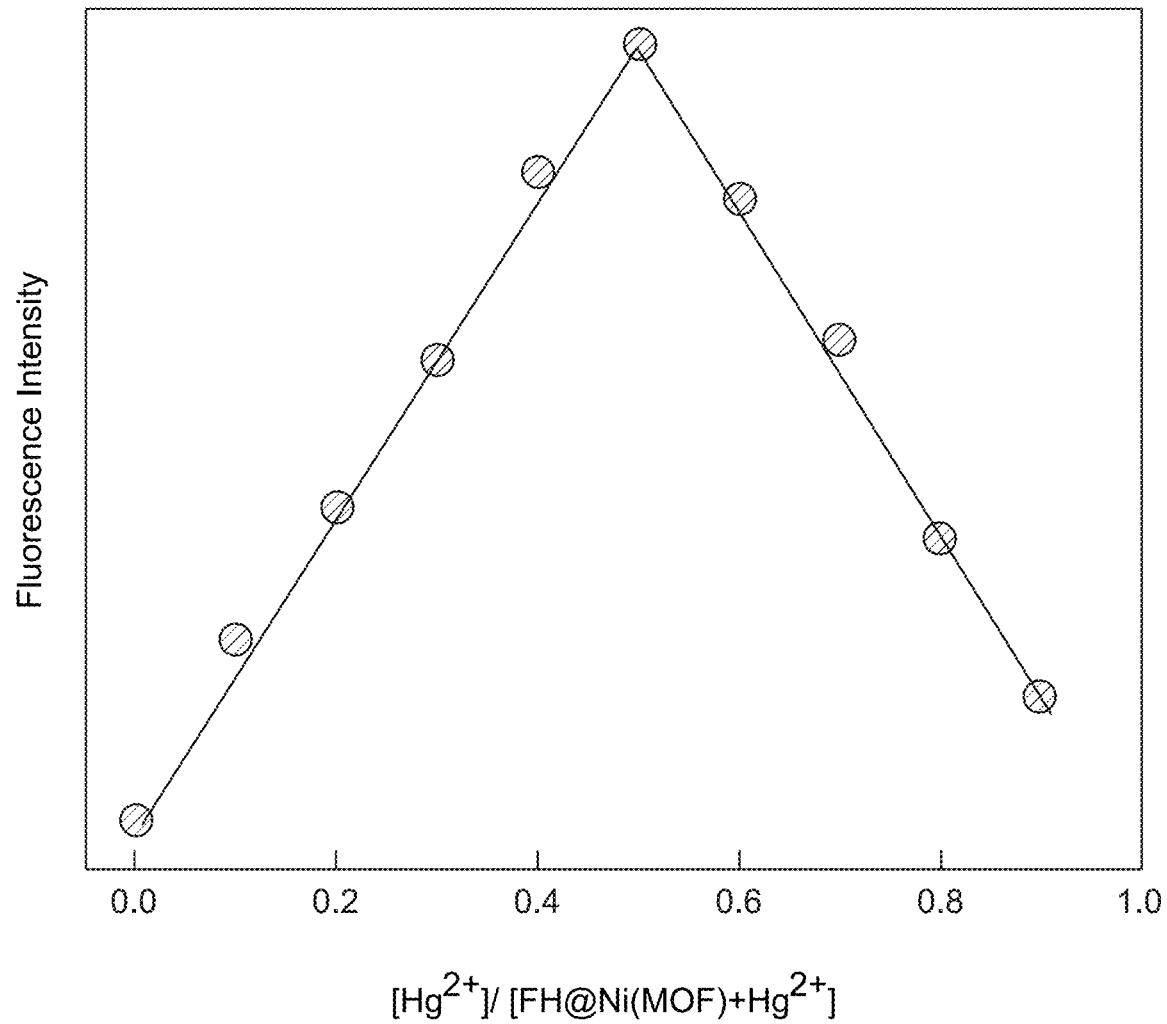
FIG. 20 shows a Job's plot for FH@Ni(MOF) with $Hg^{2+}$ in water, according to certain embodiments.
Figure 21:
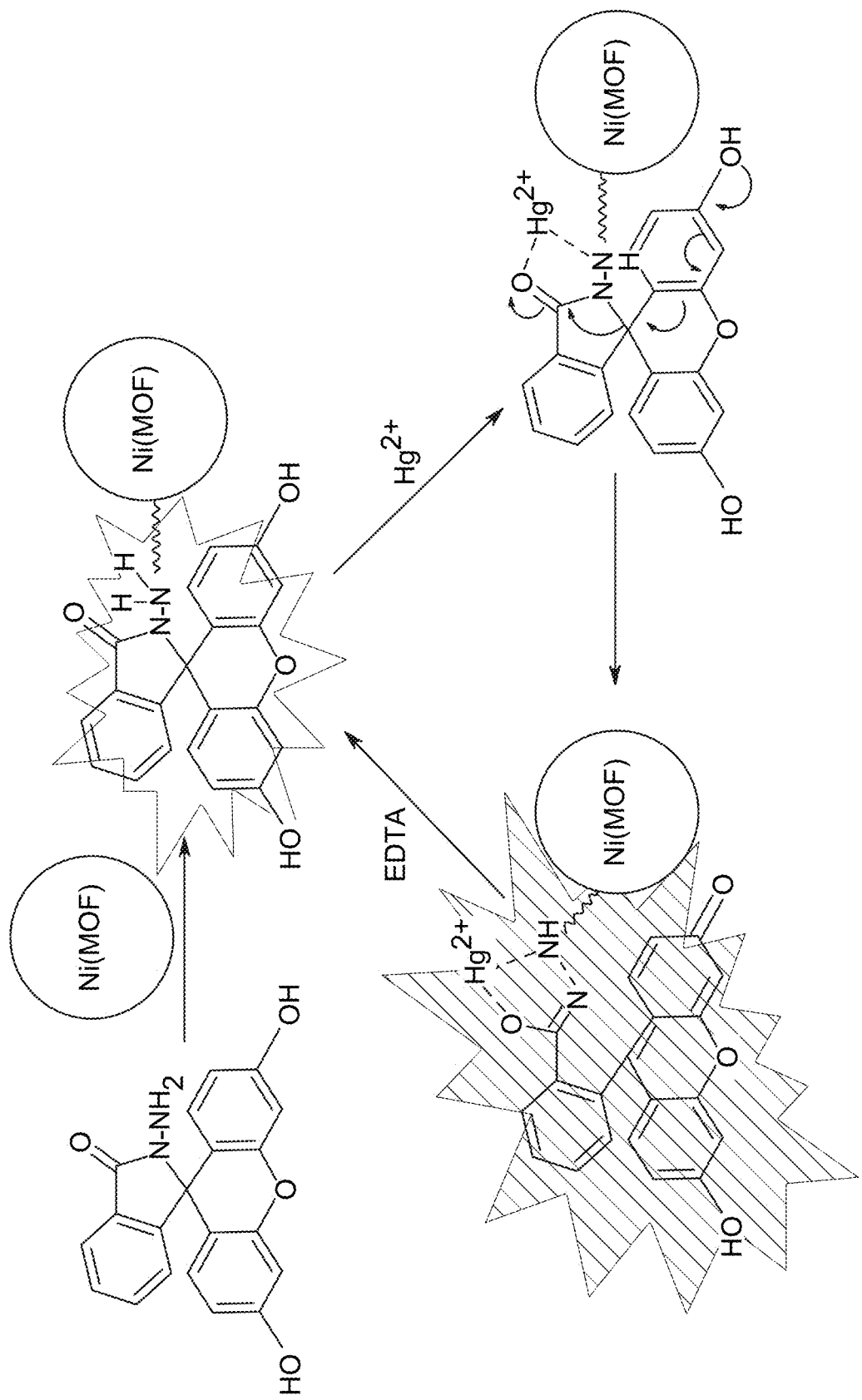
FIG. 21 shows a schematic illustration of the mechanism for the detection of $Hg^{2+}$ by FH@Ni(MOF), according to certain embodiments.
Figure 22:
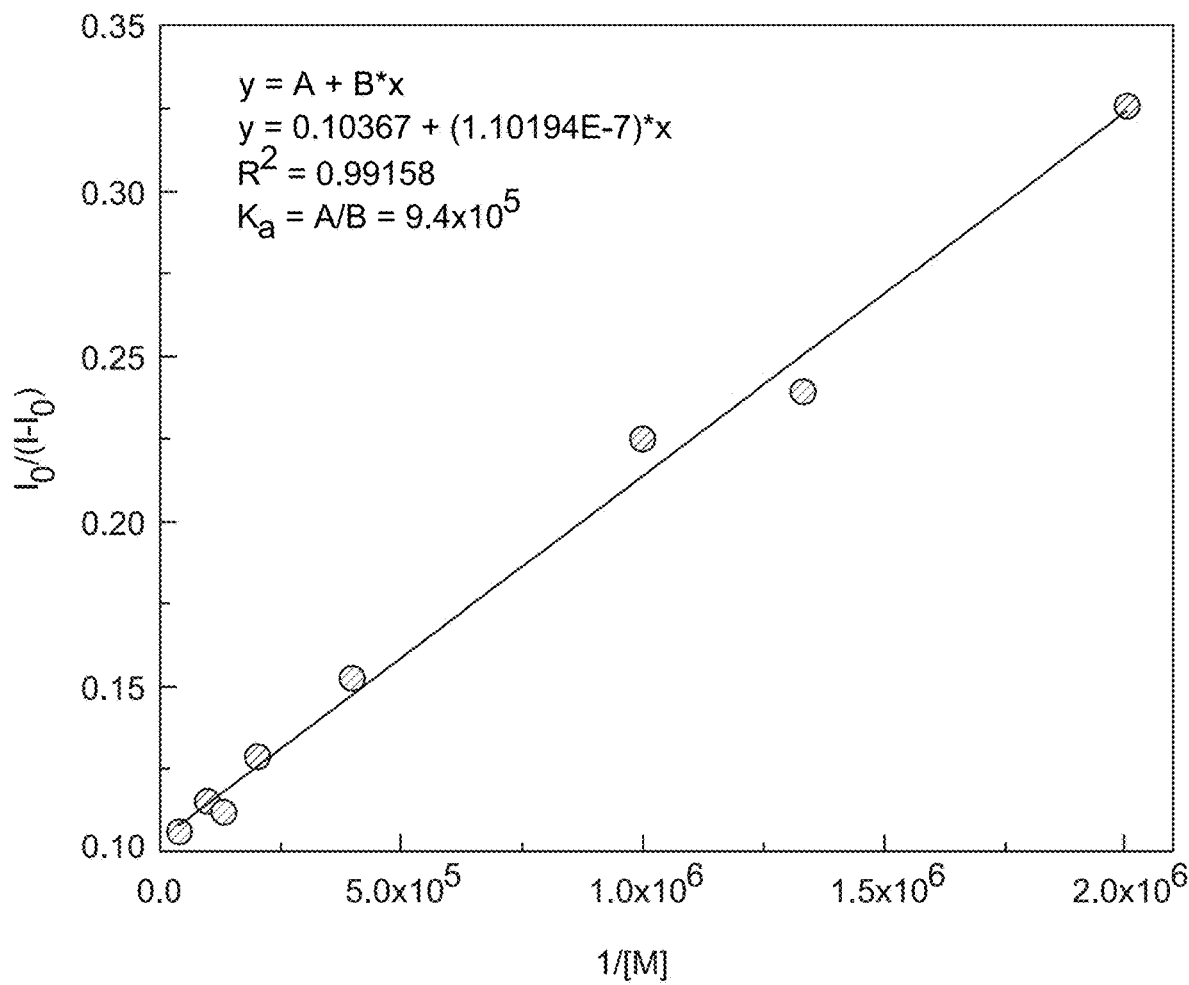
FIG. 22 shows a linear regression curve of FH@Ni(MOF) obtained by plotting emission $I_0/(I-I_0)$ as a function of $1/[Hg^{2+}]$ in an aqueous system ($\lambda_{ex}$=460 nm), according to certain embodiments.

This high selectivity is likely due to the attachment of the FH with the inorganic SBU (secondary building unit) of the Ni(MOF) in the composite FH@Ni(MOF). FIG. 19 is a plot depicting changes in fluorescence emission spectra of FH@Ni(MOF) with the incremental addition of $Hg^{2+}$ ($10^{-2}$ M) in water ($\lambda_{ex}$=460 nm). Upon the slow addition of $Hg^{2+}$ to FH@Ni(MOF) (1902), the enhancement of the peak at 523 nm upon excitation at 460 nm was observed with the change in the color of the emulsion to green fluorescence ($\lambda_{ex}$=365 nm). The augmentation of the peak at 523 nm was linear with the increase in the concentration of $Hg^{2+}$ (FIG. 19). The study was performed where the concentration of mercury ions in the sample is in range of $1\times10^{-6}$ mol/L to $2.5\times10^{-4}$ mol/L, particularly, $1\times10^{-6}$ mol/L (1904), $2.5\times10^{-6}$ mol/L (1906), $5\times10^{-6}$ mol/L (1908), $7.5\times10^{-6}$ mol/L (1910), $1\times10^{-5}$ mol/L (1912), $2.5\times10^{-5}$ mol/L (1914), $5\times10^{-5}$ mol/L (1916), $7.5\times10^{-5}$ mol/L (1918), $1\times10^{-4}$ mol/L (1920), and $2.5\times10^{-4}$ mol/L (1922), respectively. To quantify the complexation nature between the $Hg^{2+}$ and FH@Ni (MOF), the Job's plot analysis in fluorescence was executed by changing the sensor-cation concentration ratio. The maximum emission in the Job's plot occurred at the mole fraction of 0.5 or 1:1 metal to metal-MOF complex (FIG. 20). The quantum yield calculated from the integrated sphere before and after the $Hg^{2+}$ ion binding increased from 0.07 to 0.46. This indicates that the complexation of $Hg^{2+}$ with the FH@Ni(MOF) increases the charge transfer character of the composite, inhibiting the major nonradiative decay pathway. The binding constant between the metal ($Hg^{2+}$) and the MOF composite (FH@Ni(MOF) obtained from the fluorescence titration was calculated to be $9.4\times10^5$ $M^{-1}$ (error estimated to be about 10%) (FIG. 21 and FIG. 22).

Further, the detection limit was calculated based on the fluorescence quenching titration experiments. The fluorescence emission spectrum of FH@Ni(MOF) was measured five times, from which the standard deviation of the blank measurement was achieved. To gain the slope, the fluorescence intensity at 523 nm was plotted as a concentration of the analytes. The detection limit was calculated with the following equation (2):

$$\text{Detection limit} = 3\sigma/k \quad (2)$$

where σ is the standard deviation of blank measurement, and k is the slope between the normalized fluorescence intensity versus analytes concentrations.

TABLE 1

| S. No | Blank readings | $Hg^{2+}$ |
|---|---|---|
| 1 | Fluorescence Intensity | 14.2862 |
| 2 | Fluorescence Intensity | 14.1745 |
| 3 | Fluorescence Intensity | 14.2356 |
| 4 | Fluorescence Intensity | 14.3421 |
| 5 | Fluorescence Intensity | 14.2928 |
| 6 | Fluorescence Intensity | 14.3143 |
| | Standard deviation (σ) | 0.06023 |
| | Slope | 7.42E+06 |
| | Detection limit (3σ/m) | 0.024 mM/5.0 ppb |

Figure 23:
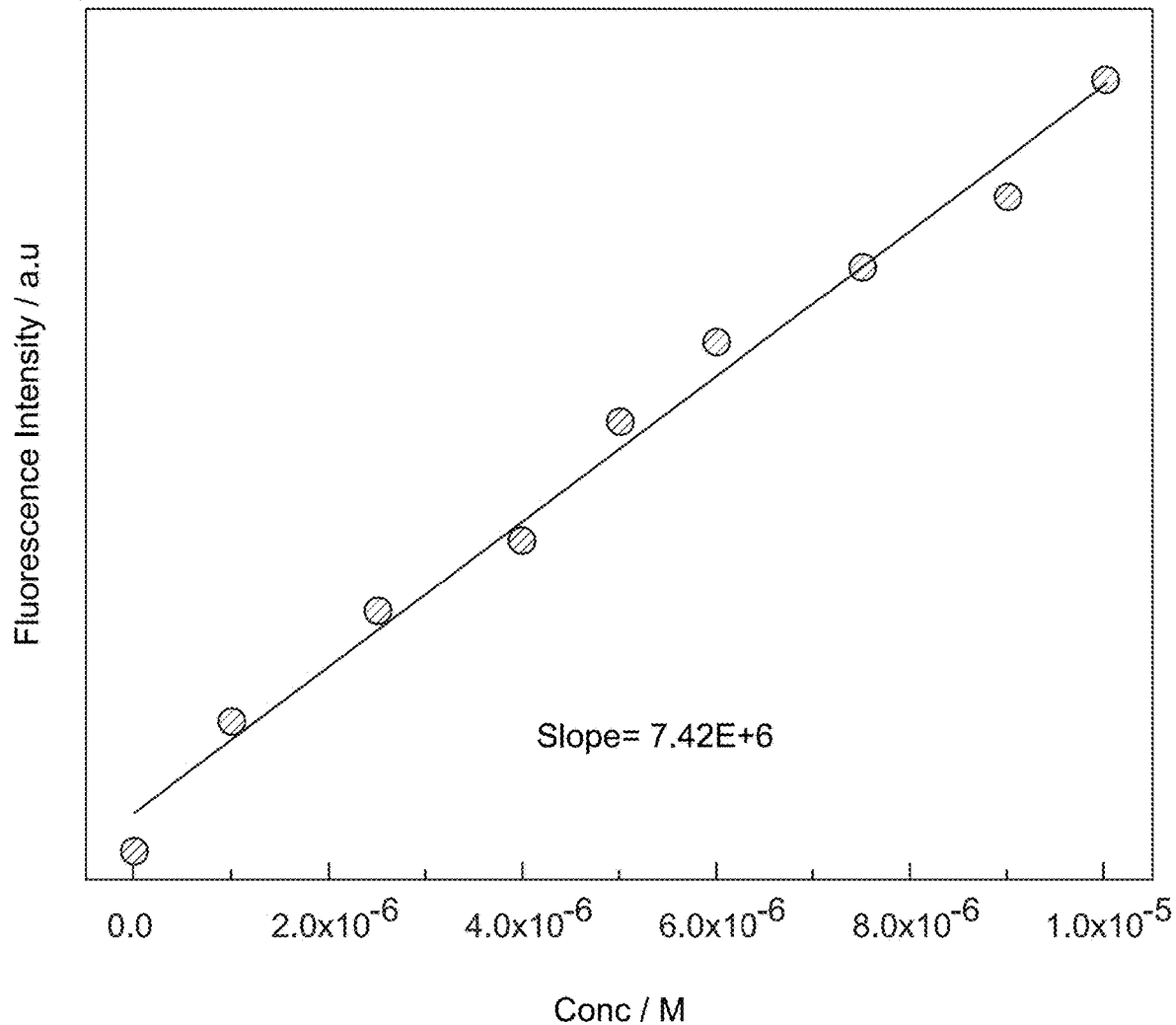
FIG. 23 shows a linear region of fluorescence intensity ($\lambda_{ex}$=460 nm and $\lambda_{ex}$=523 nm) for FH@Ni(MOF) suspensions in water upon incremental addition of $Hg^{2+}$ solutions, according to certain embodiments.

The detection limit for $Hg^{2+}$ by this sensor was calculated to be 0.02 μM or 20 nM (5 ppb) (FIG. 23). This was found to be lower than the guidelines set by the World Health Organization (WHO) and the United States Environmental Protection Agency (US-EPA) for a maximum contaminant level of $Hg^{2+}$ in drinking water of 2-6 mg/L (10 nM to 30 nM). The powdered XRD of the $Hg^{2+}$ bounded FH@Ni (MOF) indicates that the crystallinity of the MOF is intact (FIG. 7).

Figure 24:
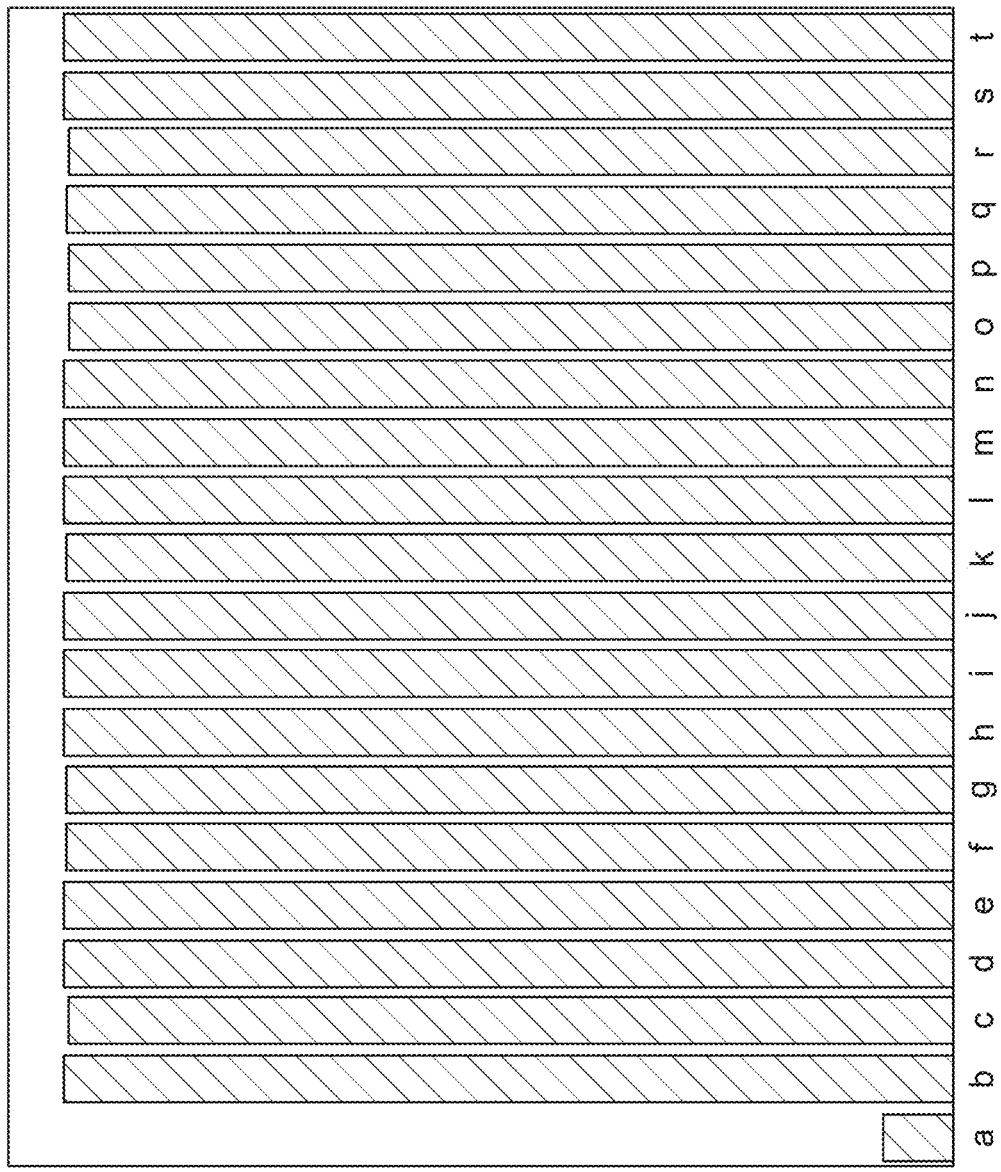
FIG. 24 is a bar graph depicting a competitive metal ion selectivity of FH@Ni(MOF) in the presence of various metal ions, according to certain embodiments.

Further, competitive binding experiments with 200 μL of various metal ions ($10^{-2}$ M) in FH@Ni(MOF) and 200 μL of the $Hg^{2+}$ ion were performed, and the results of this study are depicted in FIG. 24. For this purpose, salts of various metal ions ($10^{-2}$ M) were added to FH@Ni(MOF) and $Hg^{2+}$ ($10^{-2}$ M) (a) FH@Ni(MOF) only, (b) $Ag^+ + Hg^{2+}$, (c) $Pb^{2+} + Hg^{2+}$, (d) $Zn^{2+} + Hg^{2+}$, (e) $Mg^{2+} + Hg^{2+}$, (f) $Fe^{3+} + Hg^{2+}$, (g) $K^+ + Hg^{2+}$, (h) $Co^{2+} + Hg^{2+}$, (i) $Al^{3+} + Hg^{2+}$, (j) $Fe^{2+} + Hg^{2+}$, (k) $Na^+ + Hg^{2+}$, (l) $Cd^{2+} + Hg^{2+}$, (m) $Sr^{2+} + Hg^{2+}$, (n) $Rb^+ + Hg^{2+}$, (o) $Pd^{2+} + Hg^{2+}$ (p) $Ni^{2+} + Hg^{2+}$, (q) $Fe^{3+} + Hg^{2+}$, (r) $Ga^{3+} + Hg^{2+}$, (s) $Cs^+ + Hg^{2+}$, (t) $Ca^{2+} + Hg^{2+}$ in water. The results indicate that there was no interference by any of the metal ions in the enhancement of the emission of FH@Ni(MOF) by $Hg^{2+}$ (FIG. 24).

Figure 25:
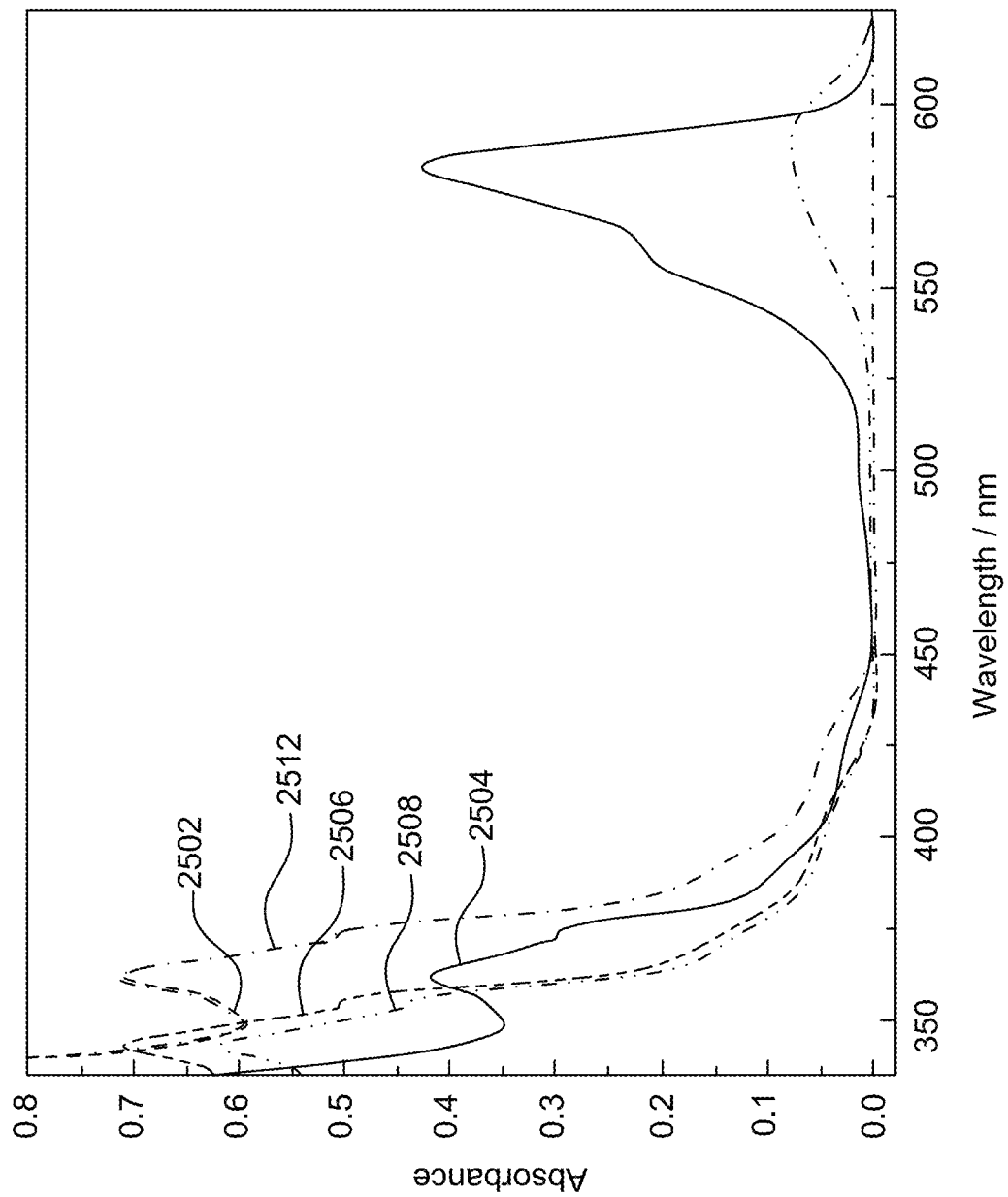
FIG. 25 shows a change in the UV-vis spectrum of FH@Ni(MOF), FH, and Ni(MOF) in water upon the addition of $Hg^{2+}$ ($10^{-2}$ M), according to certain embodiments.
Figure 26:
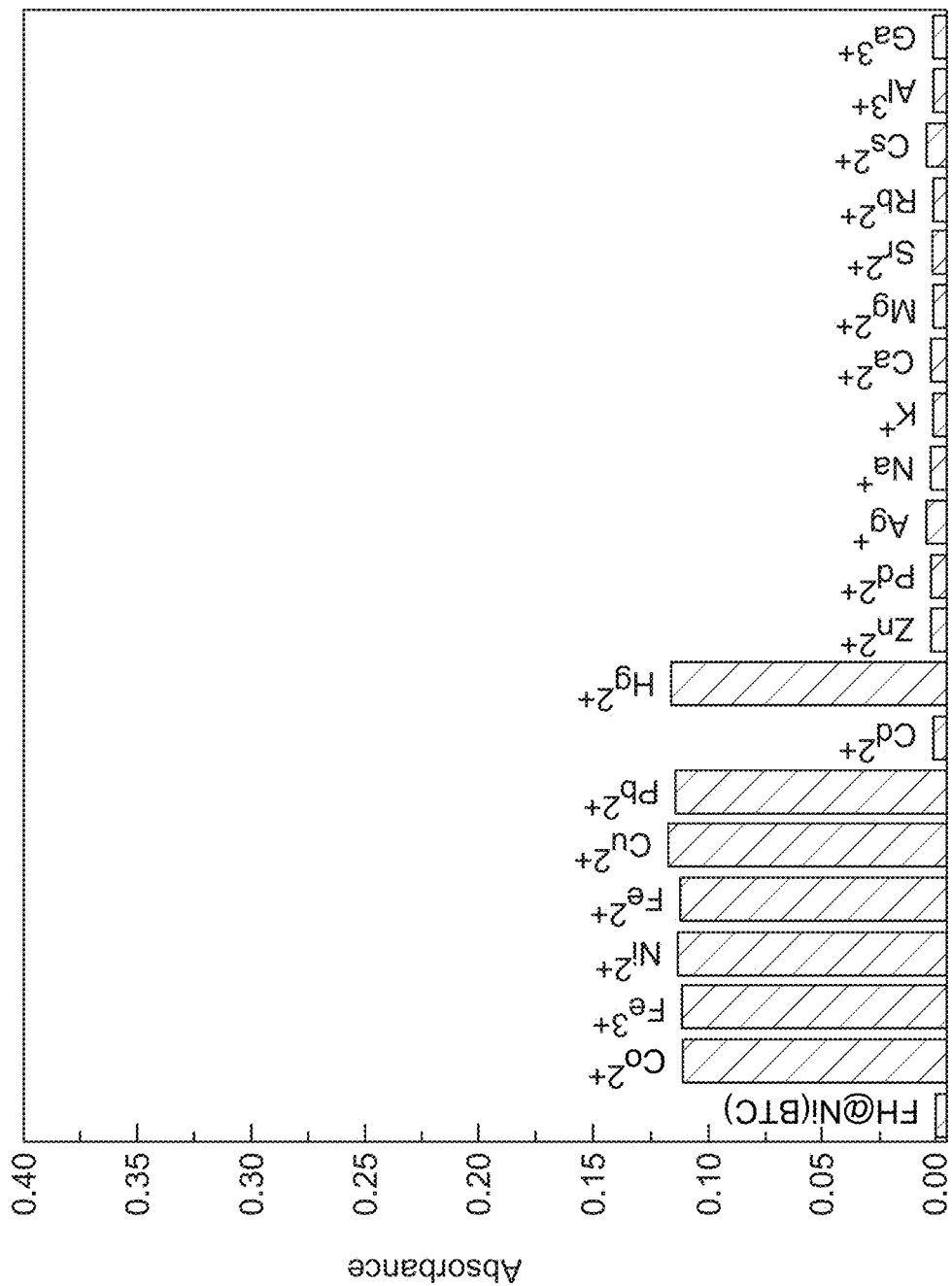
FIG. 26 shows a change in the UV-vis absorbance of FH in water upon the addition of 200 µL of different metal cations ($10^{-2}$ M), according to certain embodiments.
Figure 27:
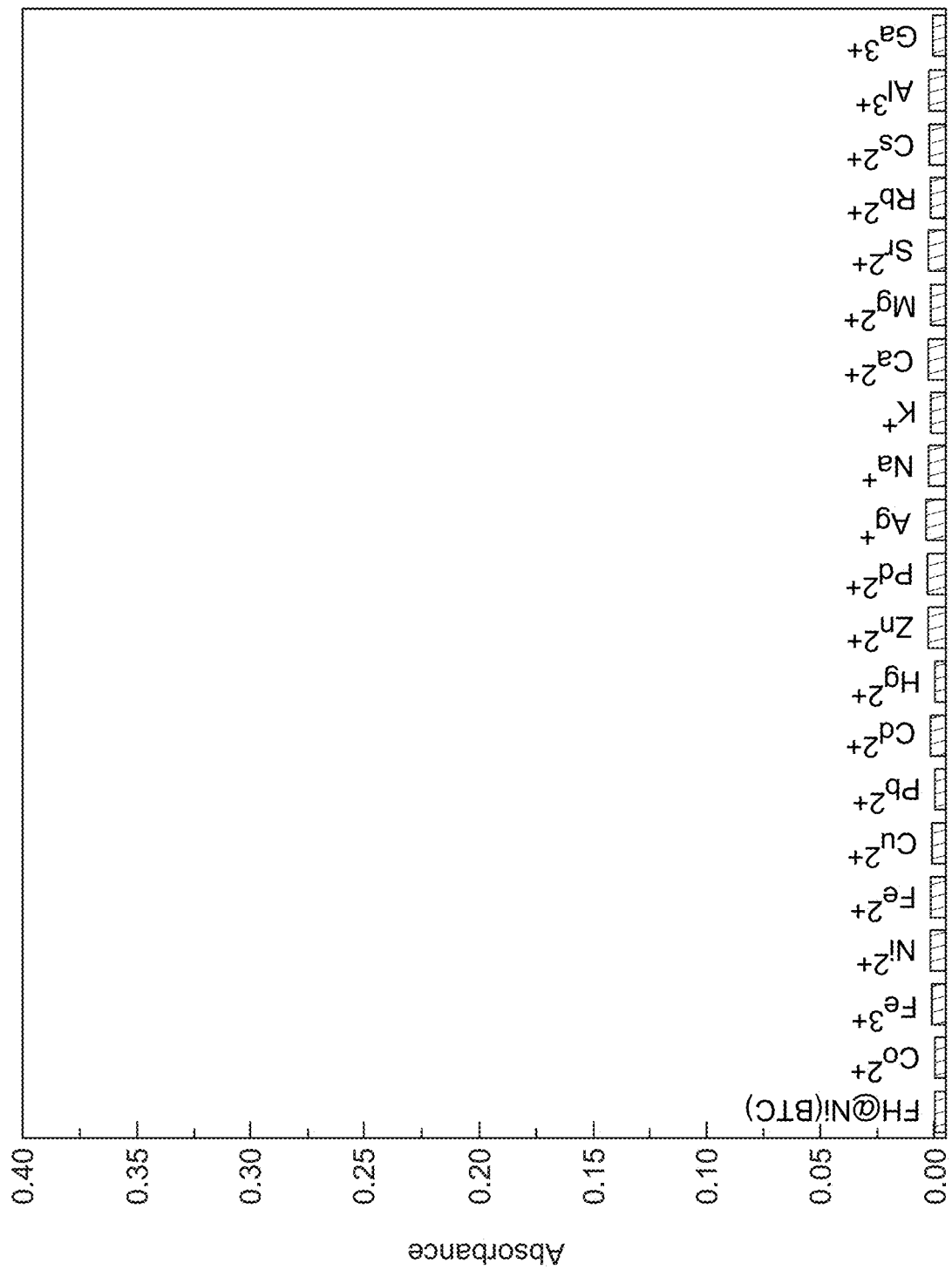
FIG. 27 shows a change in the UV-vis absorbance of Ni(MOF) in water upon the addition of 200 µL of different metal cations ($10^{-2}$ M), according to certain embodiments.

The mechanism of fluorescence can be demonstrated based on FIG. 21. FIG. 26 shows a change in the UV-vis spectrum of FH@Ni(MOF) (2502), FH (2506), and Ni(MOF) (2510), in water upon the addition of $10^{-2}$ M of $Hg^{2+}$-FH@Ni(MOF)+$Hg^{2+}$ (2502) FH+$Hg^{2+}$ (2508), and Ni(MOF)+$Hg^{2+}$ (2510). From FIG. 26, it can be observed that the binding of the $Hg^{2+}$ ion with the FH leads to the opening of the spirolactam ring, which produces a chromogenic change to a pink color that is visible to the naked eye. Moreover, the binding of the $Hg^{2+}$ ion with the FH produces the chelation enhancement of fluorescence (CHEF), resulting in the enhancement of fluorescence at 523 nm upon excitation at 460 nm. Further, the UV-V is absorbance of the Ni(MOF) and FH with different metal ions in water was studied, and the results indicate that a selective chromogenic change in absorbance is only produced by the FH@Ni(MOF) upon binding with the $Hg^{2+}$ ion (FIGS. 25-27).

Figure 28:
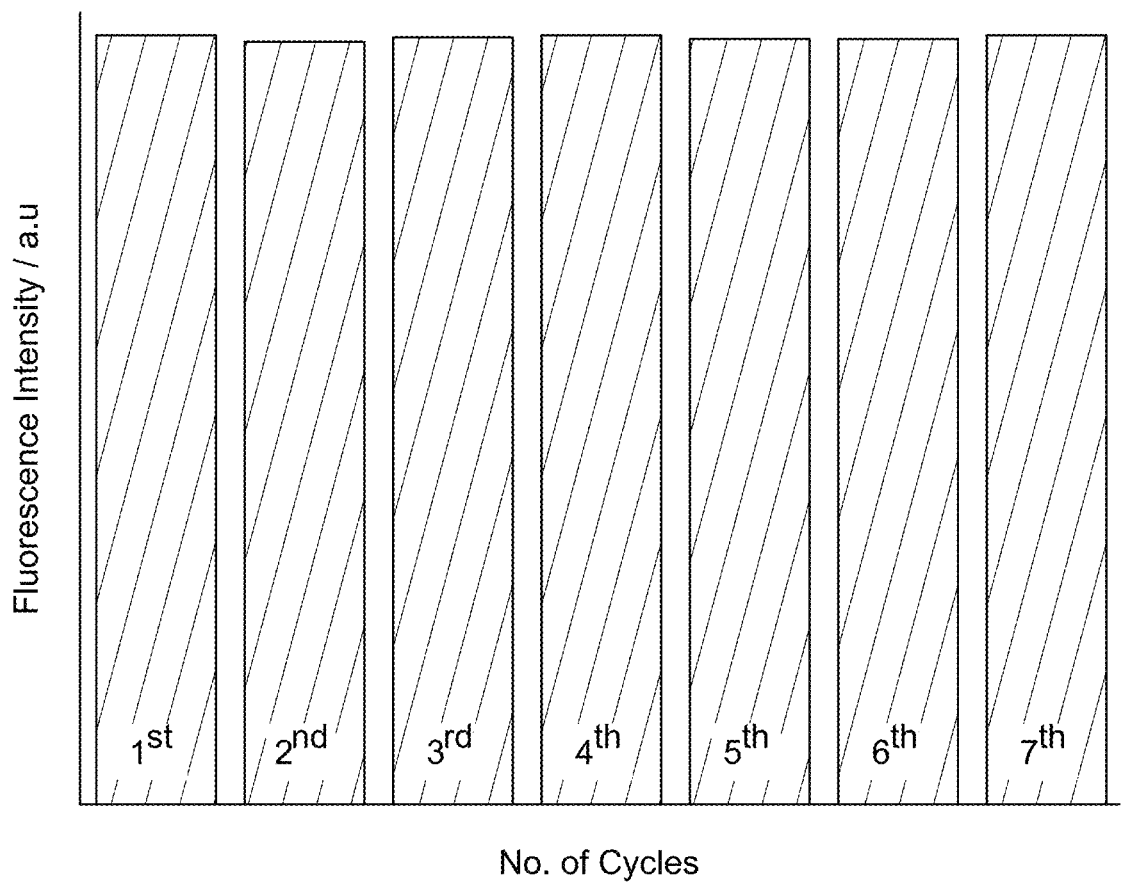
FIG. 28 shows a bar diagram depicting the recyclability of FH@Ni(MOF) on adding the $Hg^{2+}$ up to 7 cycles, according to certain embodiments.

To measure the recyclable sensing ability of FH@Ni (MOF), the fluorescence sensing experiments were repeated with the recovered materials. The first set of experiments was followed by washing with a 1.0 M aqueous solution of EDTA (ethylenediaminetetraacetic acid) to remove the bounded $Hg^{2+}$ ions and water and further drying at 100° C. for 1 h. The recovered FH@Ni(MOF) exhibited no significant change in emission intensity or sensitivity towards detecting $Hg^{2+}$ ions for seven successive cycles (FIG. 28). The FH@Ni(MOF) was further evaluated for its ability to detect $Hg^{2+}$ ions in tap water, drinking water, and groundwater using the standard addition method. FH@Ni(MOF) was used for the detection of $Hg^{2+}$ by the standard addition method. All the water samples were filtered three times through a 0.2 mm membrane filter. The results of this study are depicted in Table 2. From Table 2, the recovery yield of $Hg^{2+}$ ions ranged from 97-101%, indicating the efficacy of FH@Ni(MOF) for detecting $Hg^{2+}$ ions.

TABLE 2

Determination of $Hg^{2+}$ ions in water samples

| Sample | $Hg^{2+}$ ions (M) spiked | $Hg^{2+}$ ions (M) detected | % Recovery |
|---|---|---|---|
| Tap water | 10 | 10.09 | 100.9 |
| | 15 | 14.69 | 97.93 |
| Drinking water | 10 | 10.1 | 101 |
| | 15 | 14.58 | 97.2 |
| Ground water | 10 | 9.71 | 97.1 |
| | 15 | 14.71 | 98.07 |

The composite FH@Ni(MOF) of the present disclosure was prepared by appending fluorescein hydrazide with the inorganic SBU of Ni(MOF); and further characterized by various analytical techniques, namely, PXRD, FTIR, XPS, $N_2$ adsorption isotherm, and TGA. The composite was further evaluated for its performance as a chemosensor. The results indicate that the composite was highly selective and serves as a sensitive optical sensor for detecting $Hg^{2+}$ ions, even in the presence of other metal ions. It was observed that this composite produces a pink color visible to the naked eye and a green fluorescence upon binding with only the $Hg^{2+}$ ion; no other metal ion has such a chromogenic or fluorogenic change with this composite of the present disclosure. The binding constant was found to be $9.4 \times 10^5$ $M^{-1}$, with a detection limit of 0.02 μM or 5 ppb. The composite was also found to be reversible and could be used for seven consecutive cycles.

Numerous modifications and variations of the present disclosure are possible in light of the above teachings. Therefore, it is to be understood that the invention may be practiced otherwise than as specifically described herein within the scope of the appended claims.

The invention claimed is:
1. A method of detecting $Hg^{2+}$ ions in an aqueous solution, comprising:
   contacting the aqueous solution with a metal-organic framework (MOF) chemosensor composite to form a mixture; and
   monitoring a change in an absorption and/or a fluorescence profile of the MOF chemosensor composite in the mixture to determine a presence or absence of $Hg^{2+}$ ions in the aqueous solution;
   wherein the MOF chemosensor composite, comprises:
   fluorescein hydrazide (FH); and
   a MOF, comprising:
     nickel as a metal ion; and
     at least one trimesic acid (BTC) ligand;
   wherein a hydrazide group on the FH coordinates to the metal ion of the MOF.

2. The method of claim 1, wherein a unit of the MOF chemosensor composite has a formula of [Ni$_3$(BTC)$_2$(H$_2$O)$_{3-n}$(FH)$_n$] wherein n=1, 2 or 3.

3. The method of claim 1, wherein at least 90% of the nickel is Ni$^{2+}$.

4. The method of claim 1, wherein the MOF chemosensor composite has a morphology of rod-shaped structures assembled into sheets.

5. The method of claim 1, wherein the MOF chemosensor composite has a Brunauer-Emmett-Teller (BET) specific surface area of 350-450 m$^2$ g$^{-1}$.

6. The method of claim 1, wherein the MOF chemosensor composite has a stability up to 150° C.

7. The method of claim 1, wherein the MOF has at least one pore; and
wherein the fluorescein hydrazide at least partially penetrates at least one pore of the MOF.

8. The method of claim 1, further comprising:
monitoring the change in the absorption profile of the MOF chemosensor composite between 350 and 600 nm;
wherein a peak of the profile between 350 and 380 nm decreases in intensity and a peak between 550 and 600 nm increases in intensity in the presence of Hg$^{2+}$.

9. The method of claim 1, further comprising:
monitoring the change in the fluorescence profile of the MOF chemosensor composite between 500 and 650 nm;
wherein a peak of the profile between 515 and 550 nm increases in intensity in the presence of Hg$^{2+}$.

10. The method of claim 1, wherein the change in the absorption and/or fluorescence profile linearly correlates with the concentration of Hg$^{2+}$ in the aqueous solution.

11. The method of claim 1, further comprising quantifying the change in the absorption and/or fluorescence profile to determine a concentration of Hg$^{2+}$ ions in the aqueous solution.

12. The method of claim 1, wherein the aqueous solution further comprises at least one metal cation selected from the group consisting of Na$^+$, K$^+$, Ca$^{2+}$, Mg$^{2+}$, Sr$^{2+}$, Rb$^{2+}$, Cs$^{2+}$, Al$^{3+}$, Ga$^{3+}$, Fe$^{2+}$, Fe$^{3+}$, Cu$^{2+}$, Ni$^{2+}$, Pb$^{2+}$, Cd$^{2+}$, Co$^{2+}$, Zn$^{2+}$, Pd$^{2+}$, and Ag$^+$; and
the change in the absorption and/or fluorescence profile occurs only in the presence of Hg$^{2+}$.

13. The method of claim 1, wherein the MOF chemosensor composite is selective for detecting Hg$^{2+}$ ions.

14. The method of claim 1, wherein the limit of detection for Hg$^{2+}$ ions is 1-10 ppb.

15. The method of claim 1, wherein the binding constant of the Hg$^{2+}$ to the MOF chemosensor composite is 10$^5$-10$^6$ M$^{-1}$.

16. The method of claim 1, further comprising:
adding ethylenediaminetetraacetic acid to the mixture to form a solution;
filtering the solution and drying at a temperature of 80-120° C. for at least one hour to form a recovered MOF chemosensor composite.

17. The method of claim 16, wherein the recovered MOF chemosensor composite maintains at least 90% of the crystallinity of the MOF chemosensor composite.

* * * * *